(12) United States Patent
Martin et al.

(10) Patent No.: US 9,328,124 B2
(45) Date of Patent: May 3, 2016

(54) BACE INHIBITORS

(71) Applicant: Eli Lilly and Company, Indianapolis, IN (US)

(72) Inventors: Fionna Mitchell Martin, Berkshire (GB); Dustin James Mergott, Zionsville, IN (US); William Martin Owton, Surrey (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/427,648

(22) PCT Filed: Oct. 17, 2013

(86) PCT No.: PCT/US2013/065418
§ 371 (c)(1),
(2) Date: Mar. 12, 2015

(87) PCT Pub. No.: WO2014/066132
PCT Pub. Date: May 1, 2014

(65) Prior Publication Data
US 2015/0232483 A1 Aug. 20, 2015

Related U.S. Application Data

(60) Provisional application No. 61/718,728, filed on Oct. 26, 2012.

(51) Int. Cl.
*C07D 513/04* (2006.01)
(52) U.S. Cl.
CPC .................... *C07D 513/04* (2013.01)
(58) Field of Classification Search
CPC .................................................. C07D 513/04
USPC ........................................ 544/48; 514/224.2
See application file for complete search history.

(56) References Cited

U.S. PATENT DOCUMENTS

| | | |
|---|---|---|
| 7,868,000 B2 | 1/2011 | Zhu et al. |
| 8,158,620 B2 | 4/2012 | Suzuki et al. |
| 8,198,269 B2 | 6/2012 | Motoki et al. |
| 8,278,441 B2 | 10/2012 | Mergott et al. |
| 8,450,331 B2 | 5/2013 | Zhu et al. |
| 8,629,270 B2 | 1/2014 | Lopez et al. |
| 8,841,293 B1 | 9/2014 | Green et al. |
| 2009/0209755 A1 | 8/2009 | Suzuki et al. |
| 2010/0093999 A1 | 4/2010 | Motoki et al. |
| 2010/0317850 A1 | 12/2010 | Suzuki et al. |
| 2011/0190279 A1 | 8/2011 | Hori et al. |
| 2012/0245155 A1 | 9/2012 | Yoshida et al. |
| 2014/0350245 A1 | 11/2014 | Green et al. |

FOREIGN PATENT DOCUMENTS

| | | |
|---|---|---|
| EP | 2151435 A1 | 2/2010 |
| WO | 2009131974 A1 | 10/2009 |
| WO | 2009131975 A1 | 10/2009 |
| WO | 2012093148 A1 | 7/2012 |
| WO | 2012162334 A1 | 11/2012 |
| WO | 2013151832 A1 | 10/2013 |
| WO | 2014013076 A1 | 1/2014 |

OTHER PUBLICATIONS

May, et al., "Robust Central Reduction of Amyloid-Beta in Humans with an Orally Available, Non-Peptidic Beta-Secretase Inhibitor", The Journal of Neuroscience, Nov. 16, 2011, 31(46), pp. 16507-16516.
International Search Report, PCT/US2013/065418, Nov. 25, 2013, Eli Lilly and Company.
Written Opinion of the International Searching Authority, PCT/US2013/065418, Nov. 25, 2013, Eli Lilly and Company.
U.S. Appl. No. 14/626,320, filed Feb. 19, 2015, Eli Lilly and Company.

*Primary Examiner* — Kahsay Habte
(74) *Attorney, Agent, or Firm* — Nelsen L. Lentz

(57) ABSTRACT

The present invention provides compounds of Formula I useful as BACE inhibitors in the treatment of e.g. Alzheimer's disease: wherein A is selected from the group consisting of; of; $R^1$ is H or F; $R^2$ is H, $—OCH_3$, C1-C3 alkyl; $R^3$ is H, $—CH_3$, or $—OCH_3$; and $R^4$ is H or F; or a pharmaceutically acceptable salt thereof.

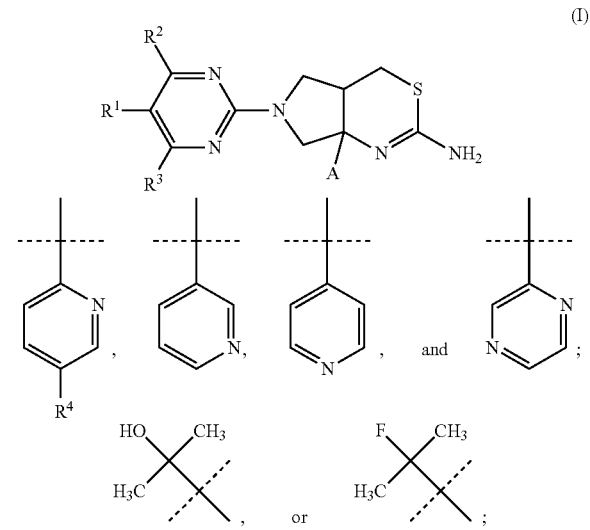

11 Claims, No Drawings

BACE INHIBITORS

The present invention relates to novel tetrahydropyrrolothiazine compounds, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Aβ) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Aβ in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in A beta peptide levels might result in a long-term significant reduction in plaque burden and synaptic deficits, thus providing significant therapeutic benefits, particularly in the treatment of Alzheimer's disease.

US 2009/0209755 discloses fused aminodihydrothiazine derivatives which are further disclosed as useful therapeutic agents for a neurodegenerative disease caused by Abeta peptide, such as Alzheimer's type dementia. In addition, *J. Neuroscience,* 31(46), pages 16507-16516 (2011) discloses (S)-4-(2,4-difluoro-5-pyrimidin-5-yl-phenyl)-4-methyl-5,6-dihydro-4H-[1,3]thiazin-2-ylamine, an orally administered CNS-active BACE inhibitor.

BACE inhibitors that are potent with sufficient CNS penetration are desired to provide treatments for Aβ peptide-mediated disorders, such as Alzheimer's disease. The present invention provides certain novel compounds that are potent inhibitors of BACE. In addition, the present invention provides certain novel compounds with CNS penetration.

Accordingly, the present invention provides compounds of Formula I:

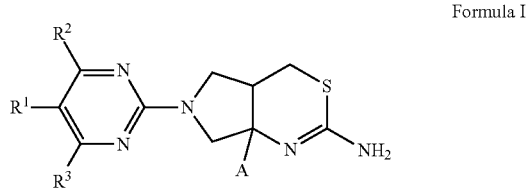

Formula I wherein A is selected from the group consisting of

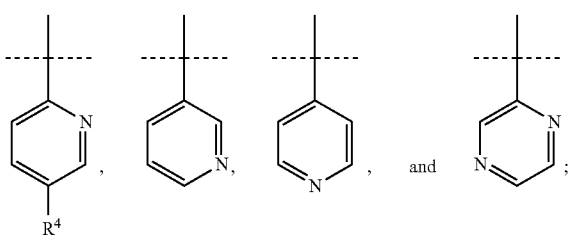

$R^1$ is H or F;
$R^2$ is H, —OCH$_3$, C1-C3 alkyl,

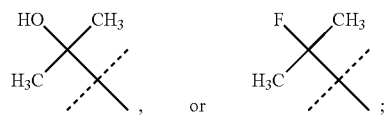

$R^3$ is H, —CH$_3$, or —OCH$_3$; and
$R^4$ is H or F;
or a pharmaceutically acceptable salt thereof.

The present invention also provides a method of treating Alzheimer's disease in a patient comprising administering to a patient in need of such treatment an effective amount of a compound of Formula I, or a pharmaceutically acceptable salt thereof.

The present invention further provides a method of preventing the progression of mild cognitive impairment to Alzheimer's disease in a patient comprising administering to a patient in need of such treatment an effective amount of a compound of Formula I, or a pharmaceutically acceptable salt thereof.

The present invention also provides a method of inhibiting BACE in a patient comprising administering to a patient in need of such treatment an effective amount of a compound of Formula I, or a pharmaceutically acceptable salt thereof.

The present invention also provides a method for inhibiting BACE-mediated cleavage of amyloid precursor protein comprising administering to a patient in need of such treatment an effective amount of a compound of Formula I, or a pharmaceutically acceptable salt thereof.

The invention further provides a method for the inhibition of production of Aβ peptide comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of Alzheimer's disease or for the prevention of the progression of mild cognitive impairment to Alzheimer's disease. Even furthermore, this invention provides the use of a compound of Formula I, or a pharmaceutically acceptable salt thereof, for the manufacture of a medicament for the treatment of Alzheimer's disease. This invention also provides the use of a compound of Formula I, or a pharmaceutically acceptable salt thereof, for the manufacture of a medicament for the prevention of the progression of mild cognitive impairment to Alzheimer's disease. The invention also provides the use of a compound of Formula I, or a pharmaceutically acceptable salt thereof, for the manufacture of a medicament for the inhibition of BACE. The invention further provides the use of a compound of Formula I, or a pharmaceutically acceptable salt thereof, for the manufacture of a medicament for the inhibition of production of Aβ peptide.

The invention further provides a pharmaceutical composition comprising a compound of Formula I, or a pharmaceutically acceptable salt thereof, with one or more pharmaceutically acceptable carriers, diluents, or excipients. In a particular embodiment, the composition further comprises one or more other therapeutic agents. This invention also encompasses novel intermediates and processes for the synthesis of the compounds of Formula I.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

As used herein, the term "C1-C3 alkyl" refers to methyl, ethyl, propyl, and isopropyl alkyl groups.

As used herein, the terms "treatment", "treating", or "to treat" includes prohibiting, preventing, restraining, slowing, stopping, or reversing the progression or severity of an existing symptom or disorder.

As used herein, the term "patient" refers to a mammal, more preferably a human.

The term "inhibition of production of Aβ peptide" is taken to mean decreasing of in vivo levels of Aβ peptide in a mammal.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way. The compounds of the invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I are particularly useful in the treatment methods of the invention, but certain groups, substituents, and configurations are preferred for compounds of Formula I. The following paragraphs describe such preferred groups, substituents, and configurations. It will be understood that these preferences are applicable both to the treatment methods and to the new compounds of the invention.

It is preferred that A is selected from the group consisting of:

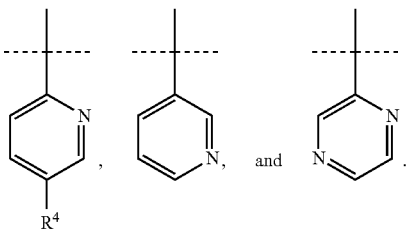

It is most preferred that A is selected from the group consisting of:

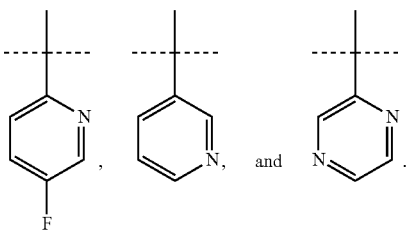

It is most especially preferred that A is:

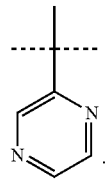

It is preferred that $R^1$ is F.

It is preferred that $R^2$ is H or

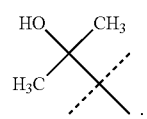

It is most preferred that $R^2$ is

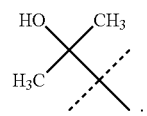

It is preferred that $R^3$ is H.

It is especially preferred that when $R^1$ is F and $R^3$ is H, that $R^2$ is H.

It is further especially preferred that when R¹ is F and R³ is H, that R² is

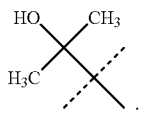

A preferred embodiment includes compounds of Formula I that have improved CNS penetration.

Preferred compounds are:
2-[2-[(4aR,7aR)-2-amino-7a-pyrazin-2-yl-4,4a,5,7-tetrahydropyrrolo[3,4-d][1,3]thiazin-6-yl]-5-fluoro-pyrimidin-4-yl]propan-2-ol;
2-[2-[(4aR,7aR)-2-amino-7a-(5-fluoro-2-pyridyl)-4,4a,5,7-tetrahydropyrrolo[3,4-d][1,3]thiazin-6-yl]-5-fluoro-pyrimidin-4-yl]propan-2-ol;
2-[2-[(4aR,7aS)-2-amino-7a-(3-pyridyl)-4,4a,5,7-tetrahydropyrrolo[3,4-d][1,3]thiazin-6-yl]-5-fluoro-pyrimidin-4-yl]propan-2-ol;
(4aR,7aR)-6-(5-fluoropyrimidin-2-yl)-7a-pyrazin-2-yl-4,4a,5,7-tetrahydropyrrolo[3,4-d][1,3]thiazin-2-amine, isomer 1; and the pharmaceutically acceptable salts thereof.

Especially preferred compounds are:
2-[2-[(4aR,7aR)-2-amino-7a-pyrazin-2-yl-4,4a,5,7-tetrahydropyrrolo[3,4-d][1,3]thiazin-6-yl]-5-fluoro-pyrimidin-4-yl]propan-2-ol;
2-[2-[(4aR,7aR)-2-amino-7a-(5-fluoro-2-pyridyl)-4,4a,5,7-tetrahydropyrrolo[3,4-d][1,3]thiazin-6-yl]-5-fluoro-pyrimidin-4-yl]propan-2-ol;
2-[2-[(4aR,7aS)-2-amino-7a-(3-pyridyl)-4,4a,5,7-tetrahydropyrrolo[3,4-d][1,3]thiazin-6-yl]-5-fluoro-pyrimidin-4-yl]propan-2-ol; and the pharmaceutically acceptable salts thereof.

A most especially preferred compound is:
2-[2-[(4aR,7aR)-2-amino-7a-pyrazin-2-yl-4,4a,5,7-tetrahydropyrrolo[3,4-d][1,3]thiazin-6-yl]-5-fluoro-pyrimidin-4-yl]propan-2-ol, and the pharmaceutically acceptable salts thereof.

One of ordinary skill in the art will appreciate that compounds of the invention can exist in tautomeric forms, as depicted in Scheme A. When any reference in this application to one of the specific tautomers of the compounds of the invention is given, it is understood to encompass both tautomeric forms and all mixtures thereof.

Scheme A

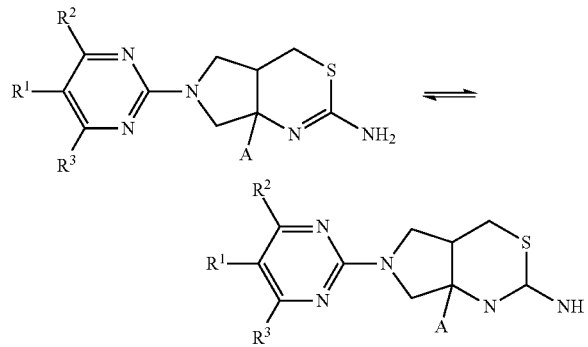

The compounds of the present invention, or salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare compounds of Formula I, or salts thereof. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of Formula I by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen,"*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples. Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

One of ordinary skill in the art will appreciate that compounds of the invention are comprised of a core that contains at least two chiral centers:

Scheme B

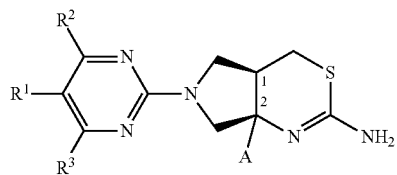

Although the present invention contemplates all individual enantiomers, as well as mixtures of the enantiomers of said compounds, including racemates, the compounds with the absolute configuration at the atoms labeled 1 and 2 as illustrated in Scheme B are preferred compounds of the invention.

Abbreviations used herein are defined according to *Aldrichimica Acta*, Vol. 17, No. 1, 1984. Other abbreviations are defined as follows: "APP" refers to amyloid precursor protein; "BOC" refers to tert-butyloxycarbonyl; "CSF" refers to cerebrospinal fluid; "DCC" refers to 1,3-dicyclohexylcarbodiimide; "DIC" refers to diisopropylcarbodiimide; "DMEM" refers to Dulbecco's Modified Eagle's Medium; "DMSO" refers to dimethylsulfoxide; "EDCI" refers to 1-(3-dimethylaminopropyl)-3-ethylcarbodiimide hydrochloride; "Ex" refers to example; "F12" refers to Ham's F12 medium; "FBS" refers to Fetal Bovine Serum; "FRET" refers to fluorescence resonance energy transfer; "HEK" refers to human embryonic kidney; "HOAc" refers to acetic acid; "HOAt" refers to 1-hydroxy-7-azobenzotriazole; "HOBt" refers to 1-hydroxylbenzotriazole hydrate; "HPLC" refers to high-performance liquid chromatography; "hr refers to hour or hours; "$IC_{50}$" refers to the concentration of an agent that produces 50% of the maximal inhibitory response possible for that agent; "min" refers to minute or minutes; "PDAPP" refers to platelet derived amyloid precursor protein; "Prep" refers to preparation; "RFU" refers to relative fluorescence unit "$R_t$" refers to retention time; and "THF" refers to tetrahydrofuran.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

pylethylamine or triethylamine and coupling reagents such as carbodiimides and HOBt or HOAt to improve the efficiency of amide coupling. One skilled in the art will recognize that there are a number of methods and reagents for amide formation resulting from the reaction of carboxylic acids and amines. For example, useful carbodiimides are DCC, DIC, EDCI.

Alternatively, the carboxylic acid can be converted to the acid chloride and the Weinreb amide can be formed using an organic base and N,O-dimethylhydroxylamine hydrochloride.

Subsequent treatment of the Weinreb amide with an organometallic reagent such as a Grignard reagent or an organolithium reagent gives compound 3, Step 2. For example, the heterocyclic halide and alkyl Grignard or organolithium reagent can be used to form a ketone with the desired (A) group attached, (3, Step 2). The ketone, (3) can then be used to form an oxime with hydroxylamine hydrochloride and an inorganic base such as sodium acetate trihydrate or sodium

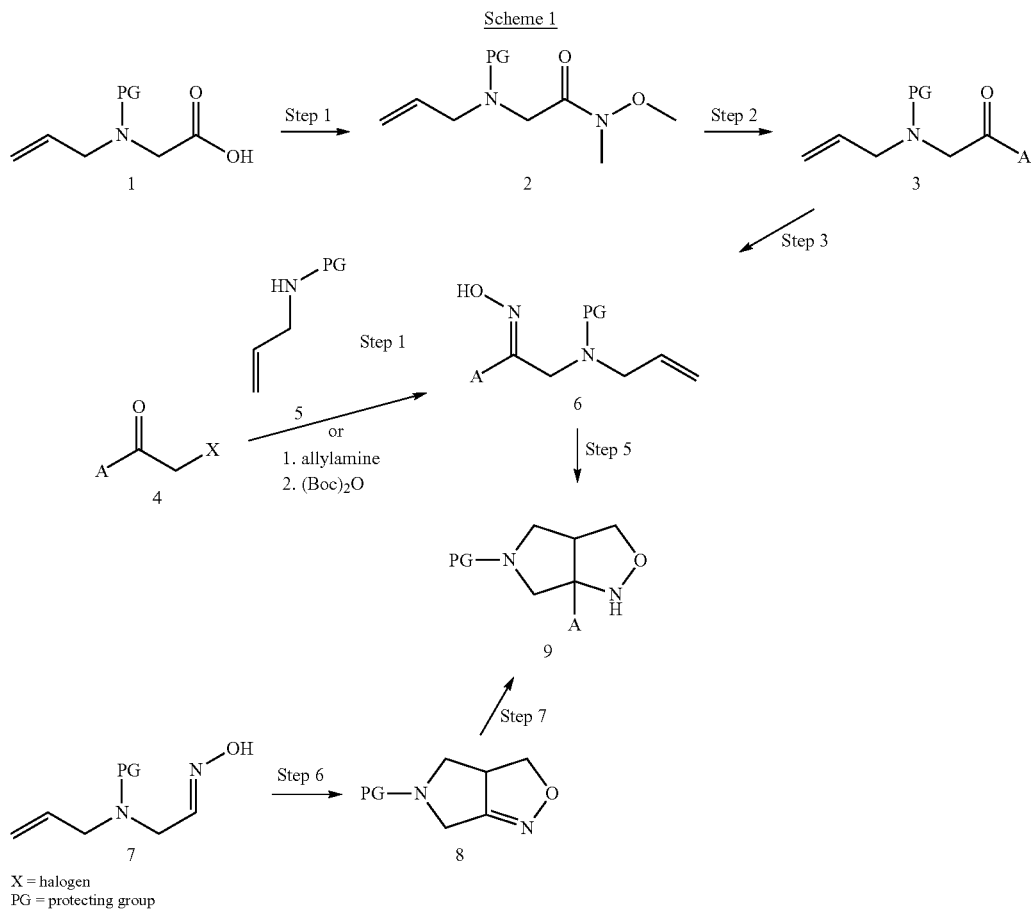

Scheme 1 depicts the formation of the Weinreb amide (2) used to form a ketone (3) that can then be transformed to an oxime. The oxime can be used to form the bicyclic isoxazole (9). The (A) group can be inserted at different points of the synthesis as shown in Scheme 1. "PG" is a protecting group developed for the amino group, such as carbamates and allyl. Such groups are well known and appreciated in the art.

A compound of formula (1) is converted to the Weinreb amide (Step 1, compound 2) with N,O-dimethylhydroxylamide hydrochloride using an organic base such as diisoproacetate or an organic base such as pyridine or by use of 50 wt % aqueous hydroxylamine solution in a polar protic solvent such as ethanol to give compound 6, Step 3. Alternatively, in a 2-step reaction, a ketone with a beta halogen can be alkylated with a protected allyl amine or by reaction with allyl amine followed by in situ tert butoxycarbamyl protection and then treated with hydroxylamine hydrochloride to give the oxime, (6, Step 4). The oxime, (6) can then be converted to the bicyclic isoxazole (9) in a 3+2 cyclization by several methods such as heating the oxime (6) in a non-polar solvent such as toluene or xylene to form compound 9, step 5 or using an aqueous solution of sodium hypochlorite or titanium (IV) ethoxide and in non-polar solvent such as toluene or xylene with heating to give compound 9, Step 5.
Scheme 2
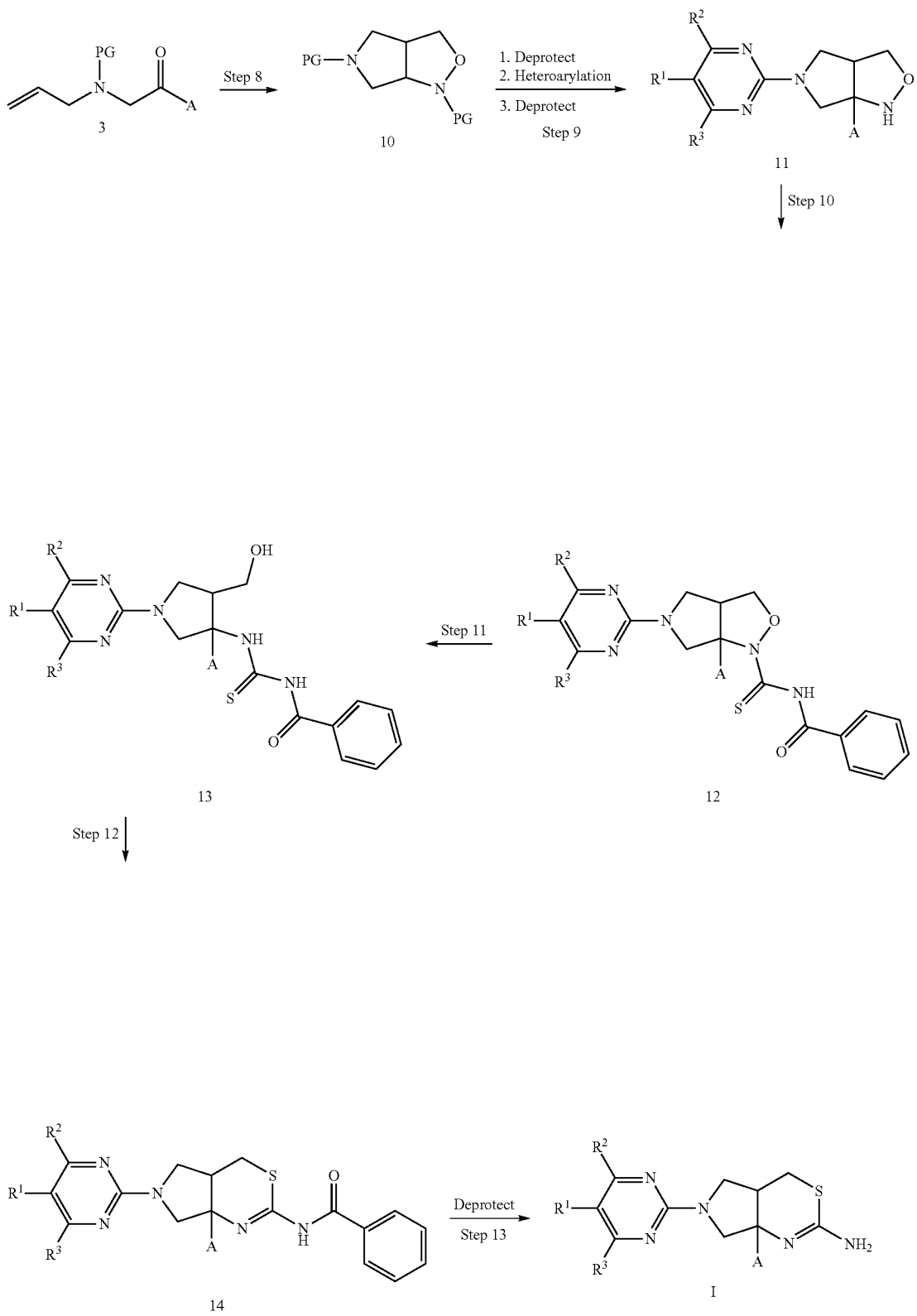

Scheme 2 illustrates the in situ formation of the oxime and subsequent conversion to form the bicyclic isoxazole to give compound (10), Step 8. N-[(4-methoxyphenylmethyl]hydroxylamine hydrochloride is treated with compound (3) in an organic base such as triethylamine to which titanium (IV) ethoxide is added and with heating gives compound 10. A BOC protected pyrrolidine of the bicyclic isoxazole is deprotected under acidic conditions well known in the art. An allyl protected pyrrolidine can be deprotected using an acid such as N,N-dimethylbarbituric acid with a catalyst such as tetrakis (triphenylphosphine)palladium. The deprotected pyrrolidine can then be reacted in a nucleophilic aromatic substitution reaction (SNAr) with a substituted or unsubstituted aromatic pyrimidine using an organic base such as diisopropylethylamine, triethylamine, or N,N,N',N'-tetramethylguanidine to give the desired substituted protected bicyclic isoxazole (Steps 1 and 2 of Step 9). The 4-methoxyl benzyl (PMB) protected bicyclic isoxazole is subsequently deprotected under acidic conditions to give compound 11, (Step 3 of Step 9). Compound 11 is treated with benzoyl isothiocyanate in a polar aprotic solvent such as THF to give the thiourea (12, Step 10). The isoxazole ring can be opened with powdered zinc in acetic acid, (13, Step 11). The hydroxy compound (13) is then treated with 1-chloro-N,N,2-trimethylpropenylamine to form the fused pyrrolidine protected thiazine (14, Step 12). The thiazine amide can be deprotected with an organic base such as pyridine and methylhydroxylamine hydrochloride in a polar aprotic solvent such as ethanol or an inorganic base such as lithium hydroxide in methanol to give compounds of Formula I in Step 13.

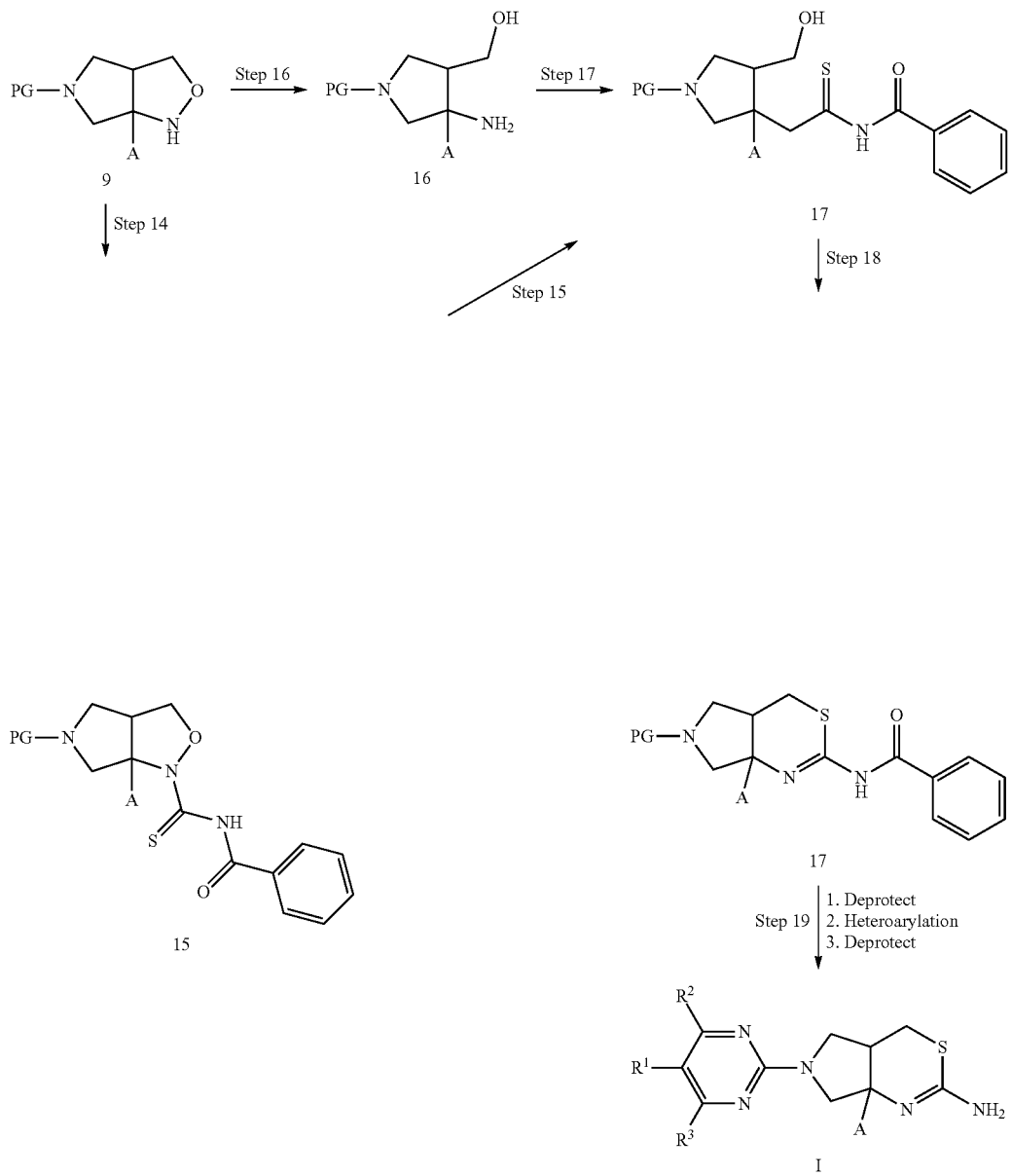

Scheme 3 depicts the protected bicyclic isoxazole (9) which can first be treated with powdered Zn in acetic acid or by Raney Nickel in a polar solvent such as ethanol under pressure hydrogenation conditions (16, Step 16) followed by reaction with benzothioisocyanate to give compound 17, Step 17. The thiazine ring can be formed as described in Scheme 2, Step 12 to give compound 18, Step 18. In Step 19, the pyrrolidine (18) can be deprotected and heteroarylated as described in Scheme 2 (Steps 1 and 2 of Step 9) to give the fused pyrrolidine protected thiazine (Compound 14, Scheme 2). The thiazine amide can then be deprotected as described in Scheme 2 (Step 13) to give compounds of Formula I.

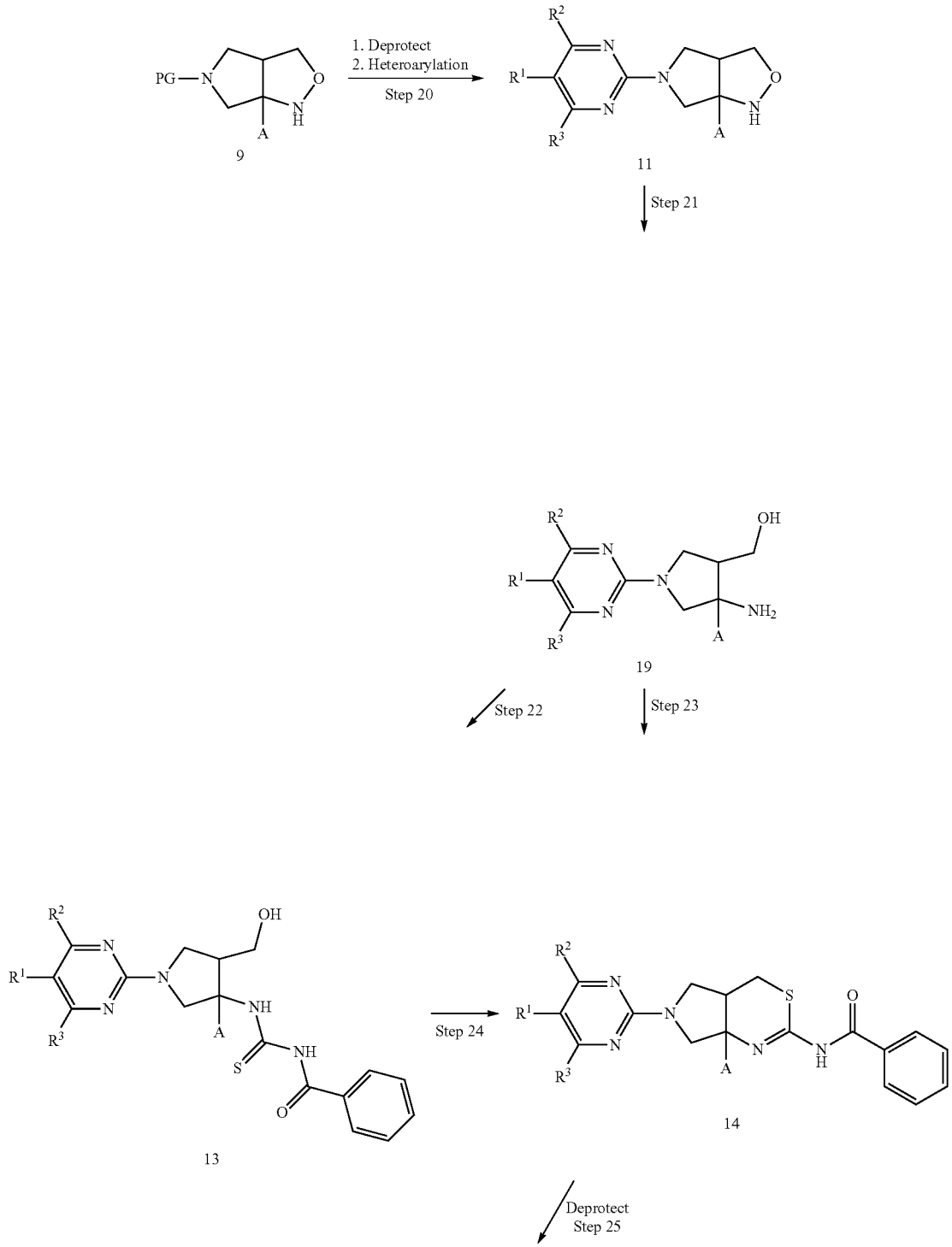

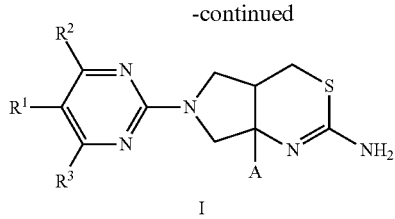

Scheme 4 depicts an alternate route from Scheme 3 and Scheme 2 in which compound 9 can be deprotected and heteroarylated in a SNAr reaction at the pyrrolidine nitrogen and the isoxazole ring can be opened before treating the bicyclic isoxazole with benzoyl isocyanate.

For example, the pyrrolidine nitrogen can be deprotected and heteroarylated as described in Scheme 2, Step 9. The isoxazole ring of compound 11 can be opened as described in Scheme 3, Step 16 to give compound 19, Step 21. A two-step conversion to form the protected thiazine, (14) can be accomplished as shown in Steps 22 and 24 and described in Steps 17 and 18, Scheme 3 or the protected thiazine can be formed directly as shown in Step 23 using benzothioisocyanate in the first step and triphenylphosphine and diisopropyl azodicarboxylate in a second step. The thiazine amide can be deprotected as described in Scheme 2, Step 13 to give compounds of Formula I.

In an optional step, a pharmaceutically acceptable salt of a compound of Formula I, such as a hydrochloride salt, can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

PREPARATIONS AND EXAMPLES

The following preparations and examples further illustrate the invention. Unless noted to the contrary, the compounds illustrated herein are named and numbered using Symyx® Draw version 3.2 (Symyx Solutions, Inc.) or IUPACNAME ACDLABS.

Preparation 1

2-Chloro-5-fluoro-4-isopropyl-pyrimidine

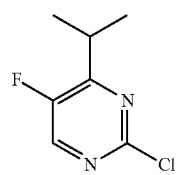

A stirred solution of 5-fluoro-2-chloropyrimidine (5.00 g, 37.7 mmol) in 1,2-dimethoxyethane (25 mL) is reacted with a solution of 2 M isopropyl magnesium chloride in tetrahydrofuran (28.3 mL, 56.6 mmol) while keeping the temperature below 15° C. The resulting solution is stirred for one hour under nitrogen and then cooled to 0° C. Triethylamine (5.76 mL, 37.7 mmol) in tetrahydrofuran (5 mL) is added followed by a solution of iodine (9.58 g, 37.7 mmol) in tetrahydrofuran (20 mL). After the addition is complete the dark reaction mixture is quenched with water followed by saturated sodium bicarbonate and saturated sodium bisulfate. The mixture is extracted with ethyl acetate (3×). The combined organic layers are dried over sodium sulfate and the solvent is removed under reduced pressure. The resulting residue is purified by silica gel column chromatography using a 5-100% gradient of dichloromethane in hexanes to give the title compound (2.55 g, 39%). GC/MS (m/e): 174.

The following compounds are prepared essentially by the method of Preparation 1.

TABLE 1

| Prep. No. | Chemical name | Structure | Physical data |
|---|---|---|---|
| 2[a] | 2-Chloro-4-ethyl-5-fluoro-pyrimidine | 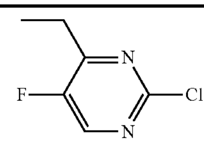 | $^1$H-NMR (CDCl$_3$) δ 1.32 (t, 3H), 2.86 (m, 2H), 8.34 (d, 1H) |
| 3[b] | 2,4-Dichloro-5-fluoro-6-methyl-pyrimidine | 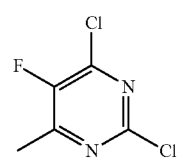 | $^1$H-NMR (CDCl$_3$) δ 2.56 (d, 3H) |

[a]Ethylmagnesium bromide (3.0M in diethylether) is used.
[b]5-Fluoro-2,4-dichloro-pyrimidine is the starting material and methylmagnesium bromide (3M in diethyl ether) is used with 1,2-dimethoxyethane as the solvent.

Preparation 4

2-Chloro-5-fluoro-4-methoxy-6-methyl-pyrimidine

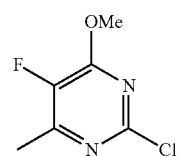

Sodium methoxide (446.53 mg, 8.27 mmol) is added portion wise to a stirred solution of 2,4-dichloro-5-fluoro-6-methyl-pyrimidine (1.7 g, 7.51 mmol) in methanol (8 mL, 197.66 mmol) at 0° C. The mixture is then stirred at room temperature for 1 hour. Water (20 mL) is added to the reaction mixture followed by dichloromethane. The layers are separated and the aqueous layer is re-extracted with dichloromethane. The combined organic extracts are dried over magnesium sulfate and the solvents are evaporated under reduced pressure to give an 8:1 of mixture of product to starting material. The crude material is purified by silica gel chromatography using a 0-99% gradient of dichloromethane in iso-hexanes to give the title compound (1.16 g, 87%). $^1$H NMR (CDCl$_3$) δ 4.09 (s, 3H), 2.45 (d, 3H).

Preparation 5

1-(2-Chloro-5-fluoro-pyrimidin-4-yl)ethanone

A room temperature solution of 5-fluoro-2,4-dichloro-pyrimidine (20 g, 119.8 mmol) and (1-ethoxyethenyl)trimethylstannane (43.26 g, 119.8 mmol) in dimethylformamide (200 mL) is purged with nitrogen. Bis(triphenylphosphine) palladium(II) chloride (1.70 g, 2.40 mmol) is added and the resulting mixture is heated to 70° C. for 2 hours under nitrogen. The reaction is cooled to 50° C. and aqueous 5 N hydrogen chloride (100 mL) is added and stirred for 2 hours. The reaction is cooled and diluted with water (200 mL) and brine and extracted five times with diethyl ether. The combined organic layers are dried over sodium sulfate and concentrated under vacuum. The crude product is purified using silica gel column chromatography using a 5-50% gradient of ethyl acetate in hexanes to give the title compound (19.2 g, 92%). GC/MS (m/e): 174 and 176.

Preparation 6

2-(2-Chloro-5-fluoro-pyrimidin-4-yl)propan-2-ol

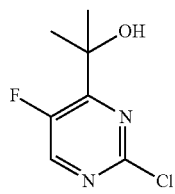

To a stirred, −78° C. solution of 1-(2-chloro-5-fluoro-pyrimidin-4-yl)ethanone (10.06 g, 57.6 mmol) in tetrahydrofuran (100 mL) under nitrogen is added methyl magnesium bromide in diethyl ether (3 M, 124 mL, 72.04 mmol) and the resulting mixture is stirred at −78° C. for 20 minutes. The reaction is quenched with aqueous saturated ammonium chloride and the mixture is warmed to room temperature. The reaction mixture is extracted three times with ethyl acetate. The combined organic layers are dried over sodium sulfate and concentrated under vacuum. The crude product is purified using silica gel column chromatography using a 5-100% gradient of ethyl acetate in hexanes to give the title compound (7.06 g, 64%). ES/MS (m/e): 191 and 193 (M+1).

Preparation 7

2-Chloro-5-fluoro-4-(1-fluoro-1-methyl-ethyl)pyrimidine

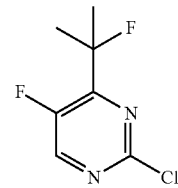

Diethylaminosulfur trifluoride (6.53 g, 40.5 mmol) is added drop wise to a −78° C. solution of 2-(2-chloro-5-fluoro-pyrimidin-4-yl)propan-2-ol (4.825 g, 25.31 mmol) in dichloromethane (70 mL) under nitrogen. The reaction is stirred at −78° C. for 30 minutes under nitrogen, quenched with saturated aqueous sodium bicarbonate, and warmed to room temperature. The reaction mixture is extracted three times with ethyl acetate. The combined organic layers are dried over sodium sulfate and concentrated under vacuum. The resulting crude product is purified using silica gel column chromatography using a 5-100% gradient of ethyl acetate in hexanes to give the title compound (4.23 g, 87%). ES/MS (m/e): 193 and 195 (M+1).

Preparation 8

(tert-Butoxycarbonylamino) tert-butyl carbonate

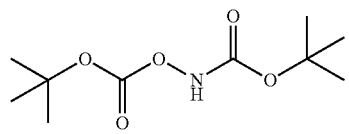 [SMILES: CC(C)(C)OC(=O)NOC(=O)OC(C)(C)C]

A mixture of hydroxylamine hydrochloride (550.0 g, 7.9 mol), water (5.5 L) and a solution of heptane/MTBE (5:1, 5.5 L) is cooled to −5° C. A pre-cooled (−5° C.) solution of di-t-butyldicarbonate (3.55 Kg, 16.3 mol), triethylamine (1.67 Kg, 16.5 mol) as a solution in heptane/MTBE (5:1, 1.1 L) is slowly added over 2 hours. The reaction is stirred at −5° C. for a 1 hour and is then warmed to room temperature and stirred overnight. The layers are separated and the organic layer is washed twice with saturated aqueous ammonium chloride (2 L) and saturated aqueous sodium chloride solution (1 L), dried over sodium sulphate, filtered, and concentrated to give an oil which crystallizes to a white solid. The solid is stirred with heptane (1 L) in an ice-water bath and filtered to give the title product (1360.2 g, 73%). $^1$H NMR (d$_6$-DMSO) δ 10.7 (bs, 1H), 1.44 (s, 9H), 1.40 (s, 9H).

Preparation 9

[tert-Butoxycarbonyl-[(4-methoxyphenyl)methyl]amino]tert-butyl carbonate

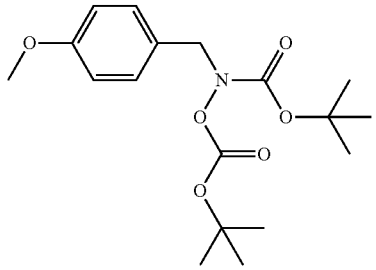 [SMILES: COc1ccc(CN(OC(=O)OC(C)(C)C)C(=O)OC(C)(C)C)cc1]

A 20 L reactor, under nitrogen is charged with (tert-butoxycarbonylamino) tert-butyl carbonate (812.9 g, 3.48 mol), dimethylformamide (4.4 L), potassium carbonate (626.5 g, 4.52 mol) and 1-(chloromethyl)-4-methoxy-benzene (462 mL, 2.56 mol). The mixture is stirred at 40° C. overnight. $^1$H NMR analysis shows incomplete reaction. Additional potassium carbonate (626.5 g, 4.52 mol) is added and the mixture is stirred at 40° C. $^1$H NMR analysis after 48 hours shows the reaction is still incomplete. Additional potassium carbonate (482 g, 3.49 mol) is added and the mixture is stirred at 40° C. $^1$H NMR analysis after overnight reaction shows complete reaction with no starting materials remaining. Water (5 L) and MTBE (5 L) are added and the layers are separated. The organic layer is washed with water (3×3 L), dried over sodium sulfate and concentrated to give compound the title compound (1.21 Kg, 98%). $^1$H NMR (d$_6$-DMSO) δ 7.20 (d, J=8.3 Hz, 2H), 6.91 (d, J=8.3 Hz, 2H), 3.73 (s, 2H), 3.35 (s, 3H), 1.41 (s, 18H).

Preparation 10

N-[(4-Methoxyphenyl)methyl]hydroxylamine hydrochloride

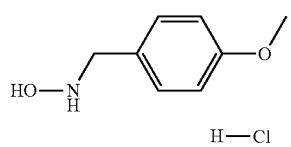

[tert-Butoxycarbonyl-[(4-methoxyphenyl)methyl]amino] tert-butyl carbonate (1.125 Kg, 3.1 mol) is dissolved in 1,4-dioxane (2.8 L) and a hydrogen chloride solution (4 M in dioxane, 3.15 L, 12.4 mol) is added drop wise over 1 hour 30 minutes. The solution is stirred at room temperature overnight. The title product is collected by filtration as white solid (488.0 g, 81%). $^1$H NMR (d$_6$-DMSO) δ 11.71 (s, 2H), 10.94 (s, 1H), 7.44 (d, J=8.8 Hz, 2H), 6.95 (d, J=8.8 Hz, 2H), 4.22 (s, 2H), 3.75 (s, 3H).

Preparation 11

2-(Allyl(tert-butoxycarbonyl)amino)acetic acid

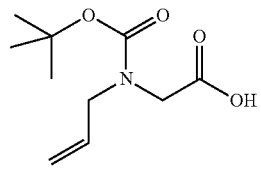

To a round bottom flask containing potassium carbonate (100 g, 724 mmol), sodium iodide (110 g, 727 mmol), dimethylformamide (300 mL), triethylamine (200 mL, 1.44 mol) and 2-propen-1-amine (24 g, 426 mmol) at 0° C. is added drop wise a solution of ethyl 2-bromoacetate (60.2 g, 360 mmol) in dimethylformamide (40 mL). The reaction is warmed to ambient temperature and stirred for 14 hours. The solids are removed by filtration and washed with diethyl ether. Saturated aqueous sodium chloride solution (1 L) is added to the filtrate and the layers are separated. The aqueous layer is extracted with diethyl ether. The organic phases are combined, dried over magnesium sulfate, filtered, and the solvent removed under reduced pressure to give a residue. To a solution at 0° C. of crude residue in ethanol (500 ml) and triethylamine (40 g, 395 mmol) is added di-t-butyldicarbonate (105 g, 467 mmol) in one portion. The reaction is warmed to room temperature and stirred for 14 hours. The reaction is concentrated under reduced pressure and is diluted with water (200 mL) and saturated aqueous sodium bicarbonate (200 mL) and extracted with diethyl ether. The organic phases are combined, dried over magnesium sulfate, filtered, and concentrated under reduced pressure to give a residue. This residue is taken up in methanol (200 mL) and 2 N sodium hydroxide (500 mL) is added. The resulting solution is stirred for 3 hours at room temperature. The volume is reduced by approximately 200 ml under reduced pressure and the resulting solution acidified to pH 4 using hydrochloric acid (12 N). The resulting pale orange solid is collected by filtration, washed with water, and dried to give the title compound (50 g, 65%). $^1$H NMR (CDCl$_3$) mixture of two rotamers (50:50) δ 1.43, 1.45 (s, 9H), 3.86-3.99 (m, 4H), 5.10-5.20 (m, 2H), 5.71-5.83 (m, 1H).

Preparation 12 tert-Butyl N-allyl-N-[2-(methoxy(methyl)amino)-2-oxo-ethyl]carbamate

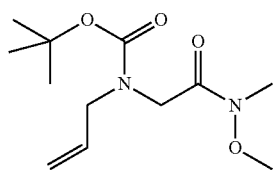 [SMILES: C=CCN(CC(=O)N(C)OC)C(=O)OC(C)(C)C]

2-(Allyl(tert-butoxycarbonyl)amino)acetic acid (49.6 g, 156 mmol) is added to tetrahydrofuran (600 mL) at 0° C.

followed by the addition of triethylamine (36.3 g, 359 mmol) and pivaloyl chloride (31 g, 353 mmol). The reaction is stirred at room temperature for 3 hours and then cooled to 0° C. N,O-dimethylhydroxylamine hydrochloride (28 g, 283 mmol), triethylamine (33 mL, 237 mmol) and tetrahydrofuran (400 mL) are then added. The ice bath is removed and the reaction stirred at room temperature for 3 hours and concentrated under reduced pressure. The resulting solid is dissolved in water and extracted with ethyl acetate. The organic phases are combined, dried over sodium sulfate, filtered, and the solvent removed under reduced pressure to give a residue. The residue is purified by silica gel column chromatography, eluting with 0-50% gradient of acetone in hexanes to give the title compound (32 g, 54%). $^1$H NMR (CDCl$_3$) mixture of two rotamers (60:40) δ 1.42, 1.44 (s, 9H), 3.16, 3.17 (s, 3H), 3.66, 3.69 (s, 3H), 3.88-3.98 (m, 2H), 4.01, 4.11 (s, 2H), 5.10-5.18 (m, 2H), 5.73-5.85 (m, 1H).

Preparation 13

2-Bromo-(3-pyridyl)ethanone hydrobromide

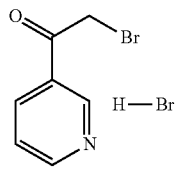

To a vigorously stirred solution of 1-(3-pyridinyl)-ethanone (7.2 mL, 65.44 mmol) in acetic acid (65 mL) and a 48% aqueous solution of hydrogen bromide (11 mL, 97.88 mmol) at 0° C. is added bromine (3.5 mL, 68.11 mmol) drop wise. The reaction is warmed to 40° C. with vigorous stirring and stirred for 2 hours. The reaction is then warmed to 75° C. and is stirred for 2 hours. The reaction mixture is cooled to room temperature and diluted with diethyl ether. The resulting precipitate is collected, washed with diethyl ether, and dried under vacuum to give the title compound as a white crystalline solid (18.27 g, 99%). $^1$H NMR (d$_6$-DMSO) δ 14.53-14.47 (m, 1H), 9.35 (d, J=1.5 Hz, 1H), 9.01 (d, J=4.9 Hz, 1H), 8.72 (d, J=7.8 Hz, 1H), 7.97-7.91 (m, 1H), 5.09 (s, 2H).

The following compound is prepared essentially by the method of Preparation 13 using 2-acetyl pyridine. Bromine is added in 4 equal portions drop wise.

TABLE 2

| Prep. No. | Chemical name | Structure | ES/MS (m/e) |
|---|---|---|---|
| 14 | 2-Bromo-1-(2-pyridyl)ethanone hydrobromide | 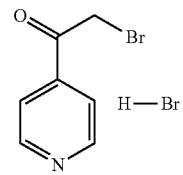 | ($^{79}$Br/$^{81}$Br) 200/202 |

Preparation 15

2-Bromo-1-(4-pyridyl)ethanone hydrobromide

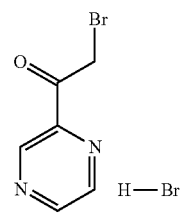

To a stirred solution of 4-acetyl pyridine (3.62 g, 29.88 mmol) in acetic acid (30 mL) is added a 48% aqueous solution of hydrogen bromide (5.3 mL, 47.16 mmol). Bromine is added (1.6 mL, 31.14 mmol) drop wise in 4 equal portions. The reaction is stirred for about 2 hours and a solid precipitated. Bromine (1.6 mL, 31.14 mmol) is added and the reaction is stirred overnight. The resulting precipitate is collected, washed with diethyl ether, and dried under vacuum to give the title compound (8.6 g, 102%). $^1$H NMR (d$_6$-DMSO) δ 9.02 (d, 2H), 8.17 (d, 2H), 5.08 (2H)

Preparation 16

2-Bromo-1-pyrazin-2-yl-ethanone hydrobromide

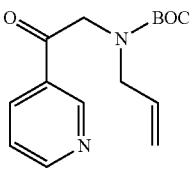 [SMILES: C=CCN(CC(=O)c1cccnc1)C(=O)OC(C)(C)C]

To a stirred solution of acetylpyrazine (10 g, 81.88 mmol) in acetic acid (70 mL) is added hydrogen bromide (38% acetic acid solution, 16 mL) followed by pyridinium bromide perbromide (28 g, 83.17 mmol) which is added in a single portion. The reaction is stirred at room temperature for approximately 1.5 hours. A suspension is formed during this time. Diethyl ether is added (500 mL) and the resulting precipitate is collected by filtration. The isolated product is washed with acetonitrile and diethyl ether and is dried under vacuum to give a pale brown solid (23.2 g, quantitative yield). $^1$H NMR (d$_6$-DMSO) δ 9.19 (1H, m), 8.95 (1H, m), 8.84 (1H, m), 5.02 (2H, s).

Preparation 17 tert-Butyl N-allyl-N-[2-oxo-2-(3-pyridyl)ethyl]carbamate

2-Bromo-1-(3-pyridyl)ethanone hydrobromide (9.35 g, 21.96 mmol) is added portion wise over 5 minutes to a stirred solution of 2-propen-1-amine (1.82 mL, 24.16 mmol) and diisopropylethylamine (7.66 mL, 43.93 mmol) in tetrahydrofuran (270 mL) at 0° C. The reaction mixture is stirred for 1 hour 40 minutes at 0° C. Di-t-butyldicarbonate (9.40 mL, 41.73 mmol) in tetrahydrofuran (10 mL) is added and the reaction is continued at 0° C. for 1 hour 40 minutes. The reaction is quenched with saturated sodium hydrogen carbonate (120 mL). Dichloromethane (300 mL) is added and the phases are separated. The aqueous phase is re-extracted with dichloromethane (300 mL). The combined organic phases are dried over magnesium sulfate, filtered, and concentrated under vacuum. The crude product is purified by silica gel chromatography using a 0-5% gradient of acetone in dichloromethane followed by a 5-10% gradient of acetone in dichloromethane then with 100% acetone to give the title compound (1.15 g, 19%). ES/MS (m/e): 277 (M+1).

The following compounds are prepared essentially by the method of Preparation 17 using the appropriate pyridine or pyrazine.

TABLE 3

| Prep. No. | Chemical name | Structure | ES/MS (m/e) |
|---|---|---|---|
| 18[a] | tert-Butyl N-allyl-N-(2-oxo-2-pyrazin-2-yl-ethyl)carbamate | 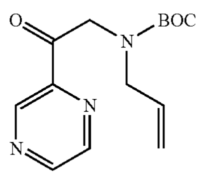 | 278 (M + 1) |
| 19[b] | tert-Butyl N-allyl-N-[2-oxo-2-(2-pyridyl)ethyl]carbamate | 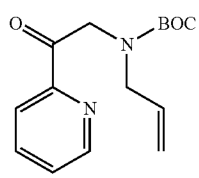 [SMILES: C=CCN(CC(=O)c1ccccn1)C(=O)OC(C)(C)C] | 277 (M + 1) |
| 20[c] | tert-Butyl N-allyl-N-[2-oxo-2-(4-pyridyl)ethyl]carbamate | 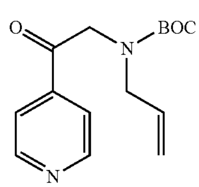 [SMILES: C=CCN(CC(=O)c1ccncc1)C(=O)OC(C)(C)C] | 277 (M + 1) |

[a]The reaction time is 70 minutes with 2-propen-1-amine and 70 minutes for tert butyl carbamate formation. Purification is by silica gel chromatography using a 0 to 10% gradient of acetone in dichloromethane.
[b]Dimethylformamide is the solvent and the reaction time is 10 minutes for reaction with 2-propen-1-amine and tert butyl carbamate formation is carried out in tetrahydrofuran/dimethylformamide. Purification is by silica gel chromatography using a 0 to 35% gradient of ethyl acetate in iso-hexanes.
[c]2-Bromo-1-(4-pyridyl)ethanone hydrobromide is added portion wise over 10 minutes and the reaction is stirred for 15 minutes at 0° C. followed by 2 hours 45 minutes minutes for tert butyl carbamate formation. Purification is by silica gel chromatography using a 0 to 5% gradient of methanol in dichloromethane.

Preparation 21 tert-Butyl N-allyl-N-[2-(5-fluoro-2-pyridyl)-2-oxo-ethyl]carbamate

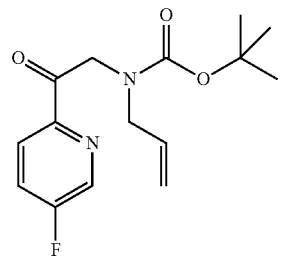 [SMILES: C=CCN(CC(=O)c1ccc(F)cn1)C(=O)OC(C)(C)C]

2-Bromo-5-fluoro-pyridine (2.46 g, 13.98 mmol) in tetrahydrofuran (20 mL) is added drop wise to isopropylmagnesium chloride (15 mL, 30.00 mmol of a 2M solution in tetrahydrofuran) with stirring under nitrogen at room temperature. The resulting reaction mixture is stirred at room temperature for 2 hours. tert-Butyl N-allyl-N-[2-[methoxy(methyl)amino]-2-oxo-ethyl]carbamate (3.4 g, 13.16 mmol) in tetrahydrofuran (15 mL) is then added drop wise at room temperature and the resulting mixture is stirred overnight. Dilute aqueous hydrochloric acid is added followed by ethyl acetate. The layers are separated and the aqueous phase is re-extracted with ethyl acetate. The combined organic extracts are dried over magnesium sulfate, filtered, and concentrated to dryness under reduced pressure. The resulting residue is purified by silica gel column chromatography using a 0-40% gradient of acetone in iso-hexane to give the title compound (1.27 g, 33%). ES/MS (m/e): 317 (M+23).

Preparation 22

2-(Diallylamino)-1-(3-pyridyl)ethanone

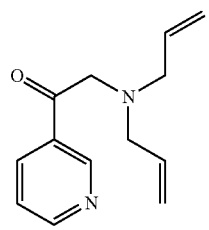 [SMILES: C=CCN(CC=C)CC(=O)c1cccnc1]

2-Bromo-1-(3-pyridyl)ethanone hydrobromide (10 g, 23.49 mmol) is added portion wise over 5 minutes to a stirred solution of diallylamine (5.2 mL, 42.29 mmol) and diisopropylethylamine (10.24 mL, 58.73 mmol) in tetrahydrofuran (150 mL) at 0° C. The resulting mixture is stirred at 0° C. for 1 hour. The reaction is quenched by addition of a saturated aqueous solution of sodium bicarbonate (100 mL) and dichloromethane (300 mL). The layers are separated and the aqueous phase is re-extracted with dichloromethane (300 mL). The combined organic layers are dried over magnesium sulfate and the solvents are removed under reduced pressure to give a crude product which is purified by silica gel column chromatography using a 0-5% gradient of 0.14 M ammonia/ methanol solution in dichloromethane to give the title compound (4.75 g, 93%). ES/MS (m/e): 217 (M+1).

Preparation 23 tert-Butyl N-allyl-N-(2-hydroxyimino-2-pyrazin-2-yl-ethyl)carbamate

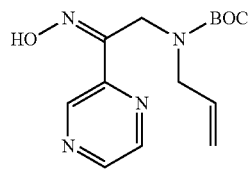 [SMILES: C=CCN(C/C(=N/O)c1cnccn1)C(=O)OC(C)(C)C]

tert-Butyl N-allyl-N-(2-oxo-2-pyrazin-2-yl-ethyl)carbamate (6.53 g, 23.55 mmol) is dissolved in ethanol (22 mL) with stirring under nitrogen. Hydroxylamine hydrochloride (3.80 g, 54.16 mmol) and pyridine (2.67 mL, 32.97 mmol) are added and the resulting solution is heated at 80° C. under nitrogen for 80 minutes. The reaction is then cooled to room temperature and is concentrated to a small volume under reduced pressure. Dichloromethane (200 ml) and 1 M aqueous sodium hydroxide (60 ml) are added and the phases are separated. The aqueous phase is re-extracted with dichloromethane (2×200 mL). The combined organic extracts are dried over magnesium sulfate and the solvent is evaporated under reduced pressure. The crude product is purified by silica gel chromatography using a 0-5% gradient of 0.14 M ammonia/methanol solution in dichloromethane to give the title compound as a mixture of E/Z isomers (6.61 g, 96%). ES/MS (m/e): 293 (M+1).

The following compound is prepared essentially by the method of Preparation 23.

Preparation 25 tert-Butyl N-allyl-N-[2-(5-fluoro-2-pyridyl)-2-hydroxyimino-ethyl]carbamate

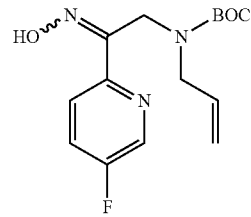 [SMILES: C=CCN(CC(=NO)c1ccc(F)cn1)C(=O)OC(C)(C)C]

2-Bromo-5-fluoro-pyridine (6.475 g, 36.79 mmol) in tetrahydrofuran (20 mL) is added drop wise to isopropylmagnesium chloride (20 mL, 40.00 mmol of a 2 M solution in tetrahydrofuran) with stirring under nitrogen at room temperature. The resulting reaction mixture is stirred at room temperature for 2 hours. tert-Butyl N-allyl-N-[2-[methoxy(methyl)amino]-2-oxo-ethyl]carbamate (4.43 g, 17.15 mmol) in tetrahydrofuran (15 mL) is then added drop wise at room temperature and the resulting mixture is stirred at room temperature for 4 hours 30 minutes. The reaction is quenched by the addition of aqueous ammonium chloride solution followed by ethyl acetate. The layers are separated and the aqueous phase is re-extracted with ethyl acetate. The combined organic extracts are dried over magnesium sulfate, filtered, and concentrated to dryness under reduced pressure. The resulting dark oil is taken up in ethanol (60 mL) with stirring. A 50 wt% aqueous solution of hydroxylamine (3 mL, 55.09 mmol) is added and the resulting solution is heated at 60° C. over the weekend. The reaction is then cooled to room temperature and is concentrated under reduced pressure. The crude product is purified by silica gel chromatography using a 0-35% gradient of isohexanes in ethyl acetate to give the

TABLE 4

| Prep. No. | Chemical name | Structure | ES/MS (m/e) |
|---|---|---|---|
| 24[a] | tert-Butyl N-allyl-N-[2-(5-fluoro-2-pyridyl)-2-hydroxyimino-ethyl]carbamate | 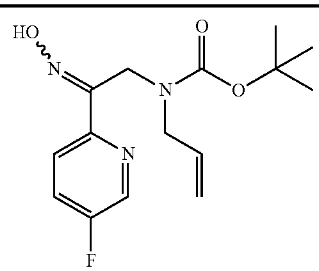 | 310 (M + 1) |

[a]The reaction is heated overnight.

title compound as a mixture of E/Z isomers (4.9 g, 92%). ES/MS (m/e): 310 (M+1).

Preparation 26 tert-Butyl 6a-pyrazin-2-yl-3,3a,4,6-tetrahydro-1H-pyrrolo[3,4-c]isoxazole-5-carboxylate

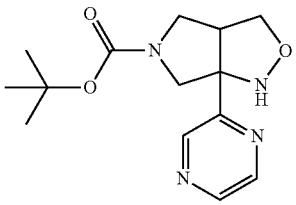 [SMILES: CC(C)(C)OC(=O)N1CC2CONC2(c2cnccn2)C1]

A solution of tert-butyl N-allyl-N-(2-hydroxyimino-2-pyrazin-2-yl-ethyl)carbamate (6.6 g, 22.58 mmol) in toluene (80 mL) is stirred at 120° C. for 22 hours. The reaction is cooled and the solvent is evaporated under reduced pressure. The crude product is purified by silica gel column chromatography using a 0-5% gradient of 0.14 M ammonia/methanol solution in dichloromethane to give the title compound (5.13 g, 74%). ES/MS (m/e): 293 (M+1).

The following compounds are prepared essentially by the method of Preparation 26.

TABLE 5

| Prep. No. | Chemical name | Structure | ES/MS (m/e) |
| --- | --- | --- | --- |
| 27[a] | tert-Butyl 6a-(5-fluoro-2-pyridyl)-3,3a,4,6-tetrahydro-1H-pyrrolo[3,4-c]isoxazole-5-carboxylate | 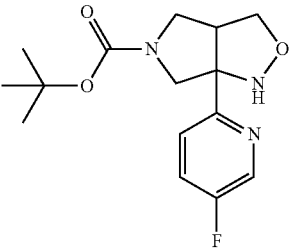 [SMILES: CC(C)(C)OC(=O)N1CC2CONC2(c2ccc(F)cn2)C1] | 310 (M + 1) |
| 28[b] | tert-Butyl 6a-(3-pyridyl)-3,3a,4,6-tetrahydro-1H-pyrrolo[3,4-c]isoxazole-5-carboxylate | 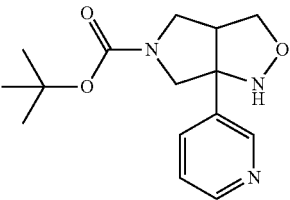 [SMILES: CC(C)(C)OC(=O)N1CC2CONC2(c2cccnc2)C1] | 292 (M + 1) |

[a]Reaction time is 3 hours 30 minutes and purification is by silica gel column chromatography using a 5-80% gradient of acetone in iso-hexanes.

[b]Reaction time is 1 hours 30 minutes at 120° C. followed by an additional 18 hours at 130° C. then at 140° C. for further days and purification is by silica gel column chromatography using a 0-10% gradient of ethanol in a 1:1 mixture of dichloromethane in isohexanes.

Preparation 29 tert-Butyl 1-[(4-methoxyphenyl)methyl]-6a-(3-pyridyl)-3,3a,4,6-tetrahydro pyrrolo[3,4-c]isoxazole-5-carboxylate

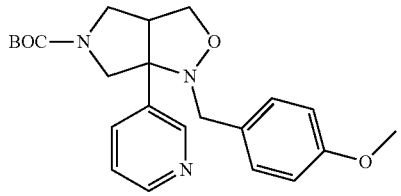 [SMILES: COc1ccc(CN2OCC3CN(C(=O)OC(C)(C)C)CC32c2cccnc2)cc1]

To a stirred solution of tert-butyl N-allyl-N-[2-oxo-2-(3-pyridyl)ethyl]carbamate (2.3 g, 8.32 mmol) in anhydrous toluene (38 mL) is added N-[(4-methoxyphenyl) methyl]hydroxylamine hydrochloride (2.05 g, 10.82 mmol) and triethylamine (1.74 mL, 12.48 mmol). Titanium (IV) ethoxide (6.09 mL, 29.13 mmol) is added and the mixture is heated at 75° C. for 5 hours. The reaction is cooled to room temperature, water (60 mL) and ethyl acetate (50 mL) are added and the mixture is stirred for 10 minutes and filtered through diatomaceous earth. The phases are separated and the organic phase is dried over magnesium sulfate, filtered, and concentrated under vacuum. The crude material is purified by silica gel chromatography using a 0-40% gradient of acetone in iso-hexanes to give the title compound (2.9 g, 76%). ES/MS (m/e): 412 (M+1).

The following compounds are prepared essentially by the method of Preparation 29 with heating varying from 2.5 hours to 6 hours.

TABLE 6

| Prep. No. | Chemical name | Structure | ES/MS (m/e) |
|---|---|---|---|
| 30[a] | tert-Butyl 1-[(4-methoxyphenyl)methyl]-6a-(2-pyridyl)-3,3a,4,6-tetrahydropyrrolo[3,4-c]isoxazole-5-carboxylate | 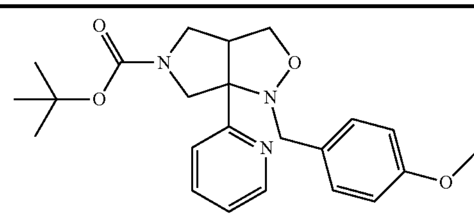 | 412 (M + 1) |
| 31 | tert-Butyl 1-[(4-methoxyphenyl)methyl]-6a-pyrazin-2-yl-3,3a,4,6-tetrahydropyrrolo[3,4-c]isoxazole-5-carboxylate | 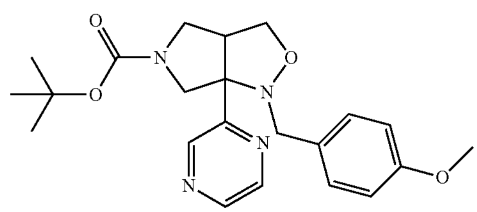 [SMILES: COc1ccc(CN2OCC3CN(C(=O)OC(C)(C)C)CC32c2cnccn2)cc1] | 413 (M + 1) |
| 32[b] | tert-Butyl 1-[(4-methoxyphenyl)methyl]-6a-(4-pyridyl)-3,3a,4,6-tetrahydropyrrolo[3,4-c]isoxazole-5-carboxylate | 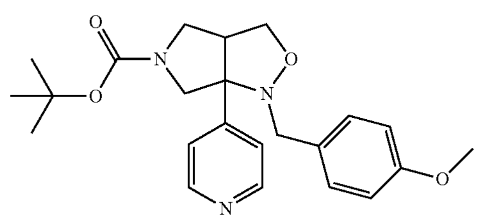 [SMILES: COc1ccc(CN2OCC3CN(C(=O)OC(C)(C)C)CC32c2ccncc2)cc1] | 412 (M + 1) |

[a]Purification is by silica gel chromatography using a 0-50% gradient of ethyl acetate in iso-hexanes.
[b]Purification is by silica gel chromatography using a 0-100% gradient of ethyl acetate in iso-hexanes.

Preparation 33

2-(Diallylamino)-1-(3-pyridyl)ethanone oxime

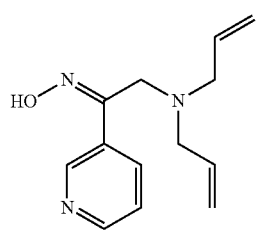 [SMILES: C=CCN(CC=C)C/C(=N/O)c1cccnc1]

2-(Diallylamino)-1-(3-pyridyl)ethanone (4.75 g, 21.96 mmol) is dissolved in ethanol (47 mL) under a nitrogen atmosphere. Hydroxylamine hydrochloride (3.55 g, 50.51 mmol) and pyridine (2.5 mL, 30.75 mmol) are then added. The resulting solution is heated at 70° C. under nitrogen for 140 minutes. The reaction is then cooled to room temperature and the solvent is partially evaporated under reduced pressure. The resulting residue is partitioned between 1 M aqueous sodium hydroxide (50 ml) and dichloromethane (250 mL). The phases are separated and the aqueous phase is re-extracted with ethyl acetate (250 mL). The organic layers are combined and the solvents are evaporated. The crude material is purified by silica gel column chromatography using a 0-10% gradient of 0.14 M ammonia/methanol solution in dichloromethane to give the title compound (3.95 g, 78%) as a mixture of E/Z isomers. ES/MS (m/e): 232 (M+1).

Preparation 34 tert-Butyl N-allyl-N-[2-hydroxyimino-2-(3-pyridyl)ethyl]carbamate

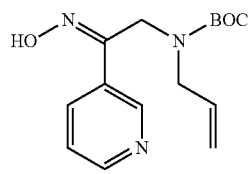 [SMILES: C=CCN(C/C(=N/O)c1cccnc1)C(=O)OC(C)(C)C]

tert-Butyl N-allyl-N-[2-oxo-2-(3-pyridyl)ethyl]carbamate (31.34 g 113.41 mmol) is dissolved in ethanol (110 mL) with stirring under nitrogen. Hydroxylamine hydrochloride (18.31 g, 260.85 mmol) and pyridine (12.84 mL, 158.78 mmol) are added. The resulting solution is heated at 80° C. under nitrogen for 2 hours and then is cooled to room temperature. The solvents are partially evaporated and the resulting residue is then partitioned between 2 M sodium hydroxide (150 ml) and dichloromethane (500 mL). The phases are separated and the aqueous phase is re-extracted with dichloromethane (2×250 mL). The organic extracts are combined and evaporated under reduced pressure. The crude product is purified by silica gel column chromatography using a gradient of 0-10% 0.14 M ammonia/methanol solution in dichloromethane to give the title compound (30.34 g, 91.82%) as a mixture of E/Z isomers. ES/MS (m/e) M+1=292.

Preparation 35

5-Allyl-6a-(3-pyridyl)-3,3a,4,6-tetrahydro-1H-pyrrolo[3,4-c]isoxazole

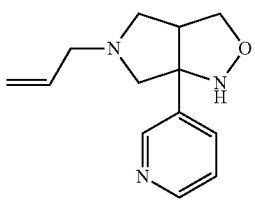 [SMILES: C=CCN1CC2CONC2(c2cccnc2)C1]

A solution of 2-(diallylamino)-1-(3-pyridyl)ethanone oxime (3.95 g, 17.08 mmol) in toluene (56 mL) is heated at 120° C. for 18 hours. The solvent is removed under reduced pressure. The crude product is purified by silica gel column chromatography using a 0-5% gradient of 0.14 M ammonia/methanol solution in dichloromethane to give the title compound (2.14 g, 43%). ES/MS (m/e): 232 (M+1).

Preparation 36

6a-(4-Pyridyl)-1,3,3a,4,5,6-hexahydropyrrolo[3,4-c]isoxazole

To a solution of tert-butyl 1-[(4-methoxyphenyl)methyl]-6a-(4-pyridyl)-3,3a,4,6-tetrahydropyrrolo[3,4-c]isoxazole-5-carboxylate (1.3 g, 3.16 mmol) in dichloromethane (30 mL) is added trifluoroacetic acid (7 mL, 94.77 mmol). The resulting solution is stirred at room temperature for 1 hour. The reaction is concentrated and the resulting residue is kept at room temperature overnight. This residue is then loaded onto an ion exchange column and the column is first eluted with methanol followed by 2 M ammonia/methanol solution. The desired basic fraction is collected and concentrated under reduced pressure to give the title compound (592 mg, 98%). ES/MS (m/e): 192 (M+1).

Preparation 37

6a-Pyrazin-2-yl-1,3,3a,4,5,6-hexahydropyrrolo[3,4-c]isoxazole

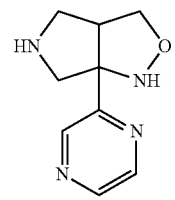 [SMILES: c1cnc(C23CNCC2CON3)cn1]

Trifluoroacetic acid (40 mL) is added to a stirred solution of tert-butyl 6a-pyrazin-2-yl-3,3a,4,6-tetrahydro-1H-pyrrolo[3,4-c]isoxazole-5-carboxylate (5.14 g, 17.58 mmol) in dichloromethane (200 mL) at room temperature. The mixture is stirred for 1 hour and the solvents are evaporated under reduced pressure. The resulting residue is dissolved in methanol (100 mL) and loaded onto an ion exchange column (50 g) and the column is first eluted with methanol (110 mL) followed by 7 M ammonia/methanol solution (150 mL). This basic fraction is concentrated under reduced pressure to give a crude product which is further purified by silica gel column chromatography using a 0-10% gradient of 0.14 M ammonia/methanol in dichloromethane to give the title compound (2.4 g, 71%). ES/MS (m/e): 193 (M+1).

The following compound is prepared essentially by the method of Preparation 37.

TABLE 7

| Prep. No. | Chemical name | Structure | ES/MS (m/e) |
|---|---|---|---|
| 38[a] | 6a-(5-Fluoro-2-pyridyl)-1,3,3a,4,5,6-hexahydropyrrolo[3,4-c]isoxazole | 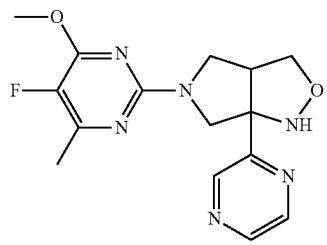 | 210 (M + 1) |

[a]Reaction time is 2 hours and purification is by ion exchange column first eluting with methanol followed by 2M ammonia/methanol solution.

Preparation 39

6a-(3-Pyridyl)-1,3,3a,4,5,6-hexahydropyrrolo[3,4-c]isoxazole

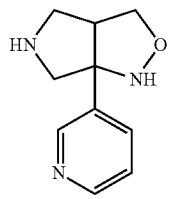 [SMILES: c1cncc(C23CNCC2CON3)c1]

5-Allyl-6a-(3-pyridyl)-3,3a,4,6-tetrahydro-1H-pyrrolo[3,4-c]isoxazole (2.14 g, 7.40 mmol) and N,N-dimethylbarbituric acid (6.93 g, 44.41 mmol) are dissolved in chloroform (80 mL) and the resulting solution is degassed twice using liquid nitrogen. Tetrakis(triphenylphosphine)palladium (1.28 g, 1.11 mmol) is added and the mixture is stirred at room temperature for 2 hours. The reaction is concentrated under reduced pressure. The resulting residue is dissolved in a 1:1 mixture of dimethylsulfoxide/methanol (40 ml) and the solution is loaded on an ion exchange column. The material is eluted with methanol (70 mL) then with 7 M ammonia/methanol solution (70 mL). The basic fraction is collected and concentrated under reduced pressure. The product is further purified by silica gel column chromatography using a 0-15% gradient of 0.14 M ammonia/methanol solution in dichloromethane to give the title compound (1.28 g, 86%). ES/MS (m/e): 192 (M+1).

Preparation 40

5-(5-Fluoro-4-methoxy-6-methyl-pyrimidin-2-yl)-6a-pyrazin-2-yl-3,3a,4,6-tetrahydro-1H-pyrrolo[3,4-c]isoxazole To a stirred solution of 6a-pyrazin-2-yl-1,3,3a,4,5,6-hexahydropyrrolo[3,4-c]isoxazole (1.4 g, 7.28 mmol) in 1,4-dioxane (30 mL) is added 2-chloro-5-fluoro-4-methoxy-6-methyl-pyrimidine (5.14 g, 29.13 mmol) and diisopropylethylamine (5.7 mL, 32.77 mmol). The resulting solution is heated at 110° C. for 4 hours. The reaction is cooled and concentrated under reduced pressure. The resulting residue is purified by silica gel column chromatography using a 0-5% gradient of 0.14 M ammonia/methanol solution in dichloromethane to give the title compound (0.93 g, 38%). ES/MS (m/e): 333 (M+1).

The following compounds are prepared essentially by the method of Preparation 40 using the appropriate pyrimidine with heating times varying from 4 hrs to 4.5 hrs and temperature ranging from 100-110° C.

TABLE 8

| Prep. No. | Chemical name | Structure | ES/MS (m/e) |
|---|---|---|---|
| 41 | 5-(5-Fluoro-4-isopropyl-pyrimidin-2-yl)-6a-pyrazin-2-yl-3,3a,4,6-tetrahydro-1H-pyrrolo[3,4-c]isoxazole | 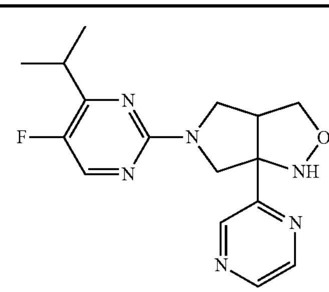 | 331 (M + 1) |

TABLE 8-continued

| Prep. No. | Chemical name | Structure | ES/MS (m/e) |
|---|---|---|---|
| 42 | 5-(5-Fluoro-4-isopropyl-pyrimidin-2-yl)-6a-(3-pyridyl)-3,3a,4,6-tetrahydro-1H-pyrrolo[3,4-c]isoxazole | 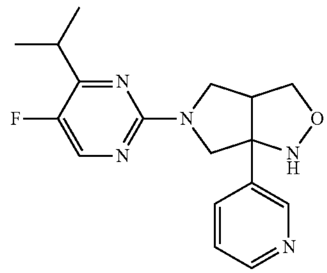 [SMILES: CC(C)c1nc(N2CC3CONC3(c3cccnc3)C2)ncc1F] | 330 (M + 1) |
| 43[a] | 6a-(5-Fluoro-2-pyridyl)-5-(5-fluoropyrimidin-2-yl)-3,3a,4,6-tetrahydro-1H-pyrrolo[3,4-c]isoxazole | 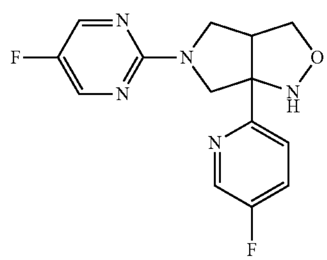 [SMILES: Fc1ccc(C23CN(c4ncc(F)cn4)CC2CON3)nc1] | 306 (M + 1) |
| 44[b] | 5-(5-Fluoropyrimidin-2-yl)-6a-(4-pyridyl)-3,3a,4,6-tetrahydro-1H-pyrrolo[3,4-c]isoxazole | 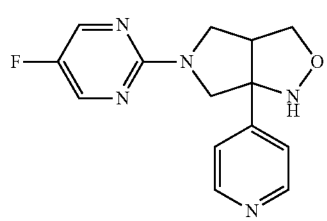 [SMILES: Fc1cnc(N2CC3CONC3(c3ccncc3)C2)nc1] | 288 (M + 1) |

[a]Purification is by silica gel column chromatography using a 0-12% gradient of 2M ammonia/methanol solution in dichloromethane.
[b]Purification is by ion exchange chromatography eluting first with methanol then with 2M ammonia/methanol to obtain the titled compound.

Preparation 45

1-[(4-Methoxyphenyl)methyl]-6a-(3-pyridyl)-3a,4,5,6-tetrahydro-3H-pyrrolo[3,4-c]isoxazole

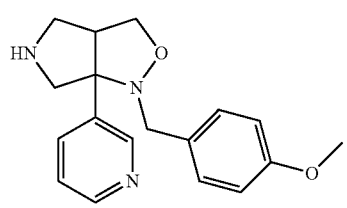 [SMILES: COc1ccc(CN2OCC3CNCC32c2cccnc2)cc1]

To a stirred solution of tert-butyl 1-[(4-methoxyphenyl)methyl]-6a-(3-pyridyl)-3,3a,4,6-tetrahydropyrrolo[3,4-c]isoxazole-5-carboxylate (2.9 g, 7.05 mmol) in dichloromethane (80 mL) is added trifluoroacetic acid (16 mL). The reaction mixture is stirred for 1 hour 30 minutes at room temperature. The solvent is concentrated and the residue is partitioned between saturated aqueous sodium bicarbonate (30 mL) and dichloromethane (100 mL). The resulting solution is stirred for 30 minutes then the phases are separated. The aqueous phase is re-extracted with dichloromethane. The combined dichloromethane extracts are dried over magnesium sulfate, filtered, and concentrated under vacuum to give a residue. The residue is purified by silica gel chromatography using a 0-10% gradient of 0.14 M ammonia/methanol solution in dichloromethane to give the title compound (1.33 g, 43%). ES/MS (m/e): 312 (M+1).

The following compound is prepared essentially by the method of Preparation 45.

TABLE 9

| Prep. No. | Chemical name | Structure | ES/MS (m/e) |
|---|---|---|---|
| 46[a] | 1-[(4-Methoxyphenyl)methyl]-6a-(2-pyridyl)-3a,4,5,6-tetrahydro-3H-pyrrolo[3,4-c]isoxazole | 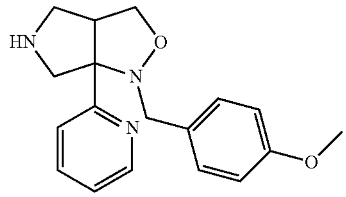 | 312 (M + 1) |
| 47[b] | 1-[(4-Methoxyphenyl)methyl]-6a-pyrazin-2-yl-3a,4,5,6-tetrahydro-3H-pyrrolo[3,4-c]isoxazole | 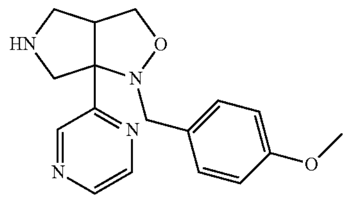 [SMILES: COc1ccc(CN2OCC3CNCC32c2cnccn2)cc1] | 313 (M + 1) |

[a]No aqueous work up, reaction is concentrated under reduced pressure and purified by ion exchange chromatography eluting with methanol then 2M ammonia/methanol solution.
[b]No aqueous work up, reaction is concentrated under reduced pressure and purified by ion exchange chromatography eluting with methanol then 2M ammonia/methanol solution to give the product which is further purified by silica gel column chromatography using a using a 0-10% gradient of 0.14M ammonia/methanol solution in dichloromethane.

Preparation 48

5-(5-Fluoropyrimidin-2-yl)-1-[(4-methoxyphenyl)methyl]-6a-(3-pyridyl)-3,3a,4,6-tetrahydropyrrolo[3,4-c]isoxazole

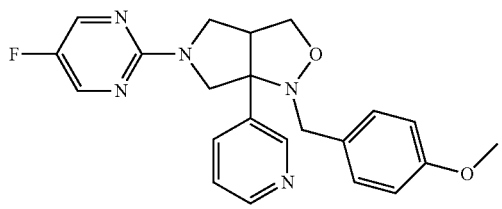 [SMILES: COc1ccc(CN2OCC3CN(c4ncc(F)cn4)CC32c2cccnc2)cc1]

To a stirred solution of 1-[(4-methoxyphenyl)methyl]-6a-(3-pyridyl)-3a,4,5,6-tetrahydro-3H-pyrrolo[3,4-c]isoxazole (1.33 g, 4.27 mmol) in 1,4-dioxane (30 mL) is added 2-chloro-5-fluoro-pyrimidine (2.55 g, 19.22 mmol) and diisopropylethylamine (3.72 mL, 21.36 mmol). The resulting solution is heated at 110° C. for 3 hours. The reaction is cooled and the solvent is evaporated under vacuum to give a residue. The residue is purified by silica gel chromatography using a 0-5% gradient of 0.14 M ammonia/methanol solution in dichloromethane to give the title compound (1.11 g, 54%). ES/MS (m/e): 408 (M+1).

The following compound is prepared essentially by the method of Preparation 48.

TABLE 10

| Prep. No. | Chemical name | Structure | ES/MS (m/e) |
|---|---|---|---|
| 49[a] | 5-(5-Fluoropyrimidin-2-yl)-1-[(4-methoxyphenyl)methyl]-6a-(2-pyridyl)-3,3a,4,6-tetrahydropyrrolo[3,4-c]isoxazole | 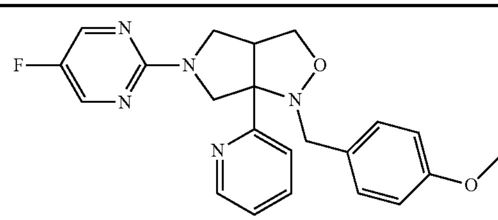 | 408 (M + 1) |
| 50 | 5-(5-Fluoropyrimidin-2-yl)-1-[(4-methoxyphenyl)methyl]-6a-pyrazin-2-yl-3,3a,4,6-tetrahydropyrrolo[3,4-c]isoxazole | 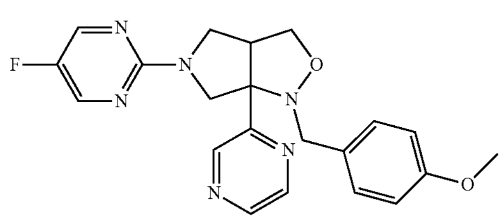 [SMILES: COc1ccc(CN2OCC3CN(c4ncc(F)cn4)CC32c2cnccn2)cc1] | 409 (M + 1) |

[a]Reaction is completed in 2 hours at 110° C. and purification is by silica gel chromatography using a 0 to 8% gradient of 2M ammonia/methanol solution in dichloromethane.

Preparation 51

5-(5-Fluoropyrimidin-2-yl)-6a-(3-pyridyl)-3,3a,4,6-tetrahydro-1H-pyrrolo[3,4-c]isoxazole

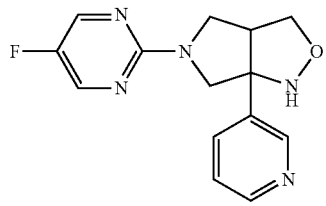 [SMILES: Fc1cnc(N2CC3CONC3(c3cccnc3)C2)nc1]

A solution of 5-(5-fluoropyrimidin-2-yl)-1-[(4-methoxyphenyl)methyl]-6a-(3-pyridyl)-3,3a,4,6-tetrahydropyrrolo[3,4-c]isoxazole (1.11 g, 2.32 mmol) in trifluoroacetic acid (9.3 mL) is stirred at 60° C. for 1 hour. The solvent is evaporated and the resulting residue is partitioned between dichloromethane (100 mL) and saturated aqueous sodium carbonate solution (25 mL). The organic phase is separated and the aqueous phase is re-extracted twice with dichloromethane (100 mL). The combined organic extracts are dried over magnesium sulfate, filtered, and the solvent evaporated under vacuum to give a residue that is purified by silica gel chromatography using a 0-10% gradient of 0.14 M ammonia/methanol solution in dichloromethane to give the title compound (0.64 g, 96%). ES/MS (m/e): 288 (M+1).

The following compounds are prepared essentially by the method of Preparation 51.

TABLE 11

| Prep. No. | Chemical name | Structure | ES/MS (m/e) |
|---|---|---|---|
| 52[a] | 5-(5-Fluoropyrimidin-2-yl)-6a-(2-pyridyl)-3,3a,4,6-tetrahydro-1H-pyrrolo[3,4-c]isoxazole | 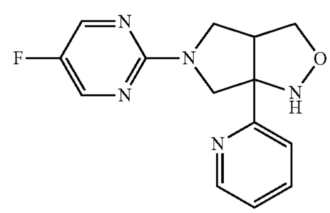 [SMILES: Fc1cnc(N2CC3CONC3(c3ccccn3)C2)nc1] | 288 (M + 1) |
| 53[b] | 5-(5-Fluoropyrimidin-2-yl)-6a-pyrazin-2-yl-3,3a,4,6-tetrahydro-1H-pyrrolo[3,4-c]isoxazole | 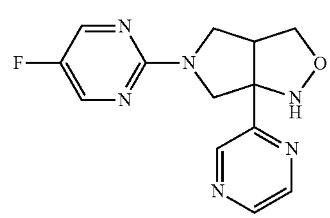 [SMILES: Fc1cnc(N2CC3CONC3(c3cnccn3)C2)nc1] | 289 (M + 1) |

[a]Purified by ion exchange chromatography eluting with tetrahydrofuran then with 7M ammonia/methanol/tetrahydrofuran solution to obtain the title compound.

[b]Purified by ion exchange chromatography eluting with methanol then with 2M ammonia/methanol solution to obtain product which was further purified by silica gel column chromatography using a using a 0-10% gradient of 0.14M ammonia/methanol solution in dichloromethane.

Preparation 54

N-[5-(5-Fluoropyrimidin-2-yl)-6a-(3-pyridyl)-3,3a,4,6-tetrahydropyrrolo[3,4-c]isoxazole-1-carbothioyl]benzamide

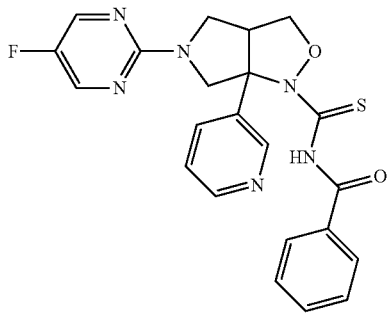 [SMILES: O=C(NC(=S)N1OCC2CN(c3ncc(F)cn3)CC21c1cccnc1)c1ccccc1]

Benzoyl isothiocyanate (511 µL 3.79 mmol) is added drop wise to a stirred solution of 5-(5-fluoropyrimidin-2-yl)-6a-(3-pyridyl)-3,3a,4,6-tetrahydro-1H-pyrrolo[3,4-c]isoxazole (640 mg, 2.23 mmol) in tetrahydrofuran (20 mL) at 0° C. The resulting mixture is stirred at 0° C. for 1 hour and is warmed to room temperature over 1 hour. The solvent is evaporated under vacuum and the resulting residue is purified by silica gel chromatography using a 0-5% gradient of 0.14 M ammonia/methanol solution in dichloromethane to give the title compound (1.1 g, quantitative). ES/MS (m/e): 451 (M+1).

Preparation 55

N-[6-(5-Fluoropyrimidin-2-yl)-7a-(3-pyridyl)-4,4a,5,7-tetrahydropyrrolo[3,4-d][1,3]thiazin-2-yl]benzamide

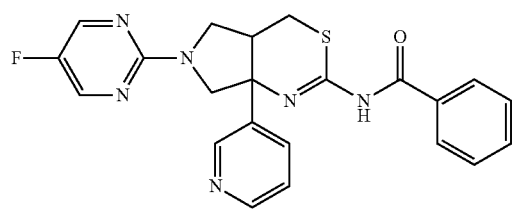

A mixture of N-[5-(5-fluoropyrimidin-2-yl)-6a-(3-pyridyl)-3,3a,4,6-tetrahydropyrrolo[3,4-c]isoxazole-1-carbothioyl]benzamide (550 mg, 1.22 mmol) and powdered zinc (798.33 mg, 12.21 mmol) in acetic acid (5 mL) is sonicated for 2 hours at room temperature. The mixture is extracted with ethyl acetate (100 mL) and a saturated aqueous sodium bicarbonate solution (30 mL). The aqueous phase is re-extracted three times with dichloromethane (100 mL). The combined organic extracts are dried over magnesium sulfate, filtered, and concentrated to give a residue. The residue is purified by silica gel chromatography using a 0-10% gradient of 0.14 M ammonia/methanol solution in dichloromethane to give the intermediate N-[[1-(5-fluoropyrimidin-2-yl)-4-(hydroxymethyl)-3-(3-pyridyl)pyrrolidin-3-yl]carbamothioyl]benzamide (145 mg). This is dissolved in dichloromethane (6 mL) and is cooled to 0° C. 1-Chloro-N,N,2-trimethylpropenylamine (0.05 g, 374.19 µmol) is then added and the mixture stirred at 0° C. for 1 hour. A saturated aqueous sodium bicarbonate solution (10 mL) and dichloromethane (100 mL) are added. The phases are separated and the organic phase is dried over magnesium sulfate, filtered, and concentrated. The residue is purified by silica gel chromatography using a 0-5% gradient of 0.14 M ammonia/methanol solution in dichloromethane to give the title product (110 mg, 17%). ES/MS (m/e): 435 (M+1).

Preparation 56

[4-Amino-1-(5-fluoro-4-methoxy-6-methyl-pyrimidin-2-yl)-4-pyrazin-2-yl-pyrrolidin-3-yl]methanol

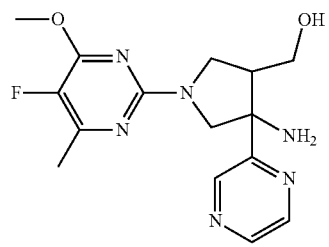 [SMILES: COc1nc(N2CC(CO)C(N)(c3cnccn3)C2)nc(C)c1F]

A solution of 5-(5-fluoro-4-methoxy-6-methyl-pyrimidin-2-yl)-6a-pyrazin-2-yl-3,3a,4,6-tetrahydro-1H-pyrrolo[3,4-c]isoxazole (0.92 g, 2.77 mmol) in ethanol (40 mL) is hydrogenated at 50 psi in the presence of Raney nickel (as a slurry in water) (2.7 g, 45.54 mmol) for 5 hours using a PARR hydrogenator. Methanol is added and the catalyst removed by filtration through a pad of diatomaceous earth. The diatomaceous earth pad is washed with methanol. The combined filtrates are concentrated under reduced pressure to give the title compound (0.92 g, 99%). ES/MS (m/e): 335 (M+1).

The following compounds are prepared essentially by the method of Preparation 56 with reaction time varying from 5 hrs to 3 days using either a PARR hydrogenator or a flow hydrogenator.

TABLE 12

| Prep. No. | Chemical name | Structure | ES/MS (m/e) |
|---|---|---|---|
| 57 | [4-Amino-1-(5-fluoro-4-isopropyl-pyrimidin-2-yl)-4-pyrazin-2-yl-pyrrolidin-3-yl]methanol | 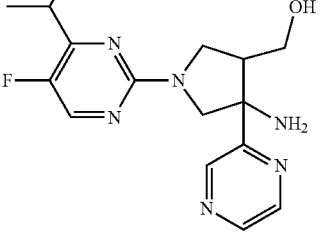 | 333 (M + 1) |
| 58 | 4-[4-Amino-1-(5-fluoro-4-isopropyl-pyrimidin-2-yl)-(3-pyridyl)pyrrolidin-3-yl]methanol | 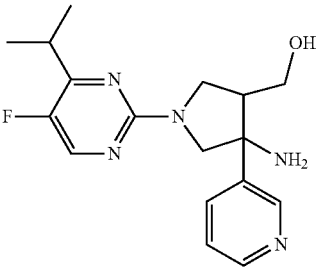 [SMILES: CC(C)c1nc(N2CC(CO)C(N)(c3cccnc3)C2)ncc1F] | 332 (M + 1) |
| 59 | tert-Butyl 3-amino-4-(hydroxymethyl)-3-pyrazin-2-yl-pyrrolidine-1-carboxylate | 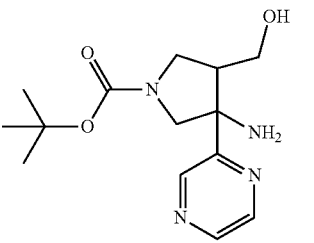 [SMILES: CC(C)(C)OC(=O)N1CC(CO)C(N)(c2cnccn2)C1] | 295 (M + 1) |
| 60 | [4-Amino-1-(5-fluoropyrimidin-2-yl)-4-(2-pyridyl)pyrrolidin-3-yl]methanol | 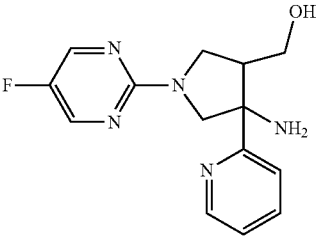 [SMILES: NC1(c2ccccn2)CN(c2ncc(F)cn2)CC1CO] | 290 (M + 1) |
| 61 | [4-Amino-4-(5-fluoro-2-pyridyl)-1-(5-fluoropyrimidin-2-yl)pyrrolidin-3-yl]methanol | 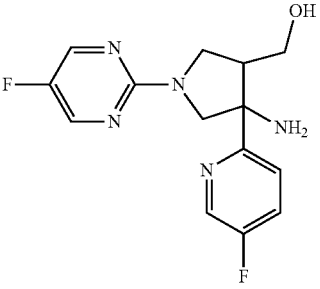 [SMILES: NC1(c2ccc(F)cn2)CN(c2ncc(F)cn2)CC1CO] | 308 (M + 1) |
| 62 | tert-Butyl 3-amino-4-(hydroxymethyl)-3-(3-pyridyl)pyrrolidine-1-carboxylate | 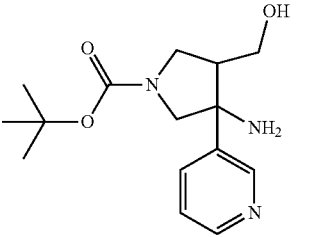 [SMILES: CC(C)(C)OC(=O)N1CC(CO)C(N)(c2cccnc2)C1] | 294 (M + 1) |

TABLE 12-continued

| Prep. No. | Chemical name | Structure | ES/MS (m/e) |
|---|---|---|---|
| 63 | [4-Amino-1-(5-fluoropyrimidin-2-yl)-4-pyrazin-2-yl-pyrrolidin-3-yl]methanol | 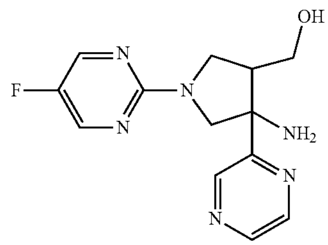 [SMILES: NC1(c2cnccn2)CN(c2ncc(F)cn2)CC1CO] | 291 (M + 1) |
| 64 | [4-Amino-1-(5-fluoropyrimidin-2-yl)-4-(4-pyridyl)pyrrolidin-3-yl]methanol | 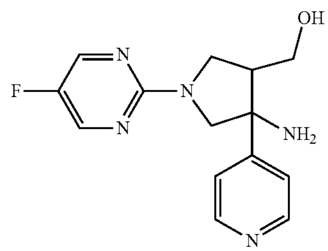 [SMILES: NC1(c2ccncc2)CN(c2ncc(F)cn2)CC1CO] | 290 (M + 1) |

Preparation 65

N-[[1-(5-Fluoro-4-methoxy-6-methyl-pyrimidin-2-yl)-4-(hydroxymethyl)-3-pyrazin-2-yl-pyrrolidin-3-yl]carbamothioyl]benzamide

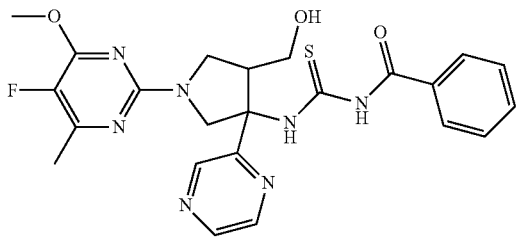 [SMILES: COc1nc(N2CC(CO)C(NC(=S)NC(=O)c3ccccc3)(c3cnccn3)C2)nc(C)c1F]

To a stirred solution of [4-amino-1-(5-fluoro-4-methoxy-6-methyl-pyrimidin-2-yl)-4-pyrazin-2-yl-pyrrolidin-3-yl]methanol (930 mg, 2.78 mmol) in tetrahydrofuran (29 mL) under a nitrogen atmosphere is added benzoyl isothiocyanate (613 µL, 4.45 mmol). After stirring the reaction at room temperature for 1 hour the solvent is removed under reduced pressure. The resulting residue is purified by silica gel column chromatography using a 0-5% gradient of 0.14 M ammonia/methanol solution in dichloromethane to give the title compound (1.32 g, 95%). ES/MS (m/e): 498 (M+1).

The following compounds are prepared essentially by the method of Preparation 65.

TABLE 13

| Prep. No. | Chemical name | Structure | ES/MS (m/e) |
|---|---|---|---|
| 66 | N-[[1-(5-Fluoro-4-isopropyl-pyrimidin-2-yl)-4-(hydroxymethyl)-3-pyrazin-2-yl-pyrrolidin-3-yl]carbamothioyl]benzamide | 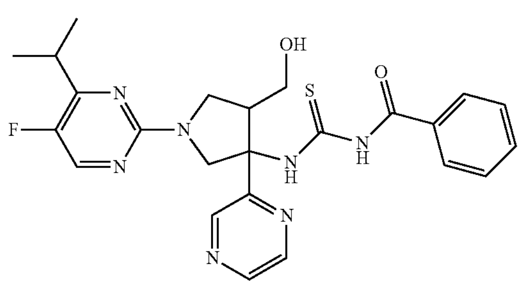 [SMILES: CC(C)c1nc(N2CC(CO)C(NC(=S)NC(=O)c3ccccc3)(c3cnccn3)C2)ncc1F] | 496 (M + 1) |

TABLE 13-continued

| Prep. No. | Chemical name | Structure | ES/MS (m/e) |
|---|---|---|---|
| 67[a] | N-[[1-(5-Fluoro-4-isopropyl-pyrimidin-2-yl)-4-(hydroxymethyl)-3-(3-pyridyl)pyrrolidin-3-yl]carbamothioyl]benzamide | 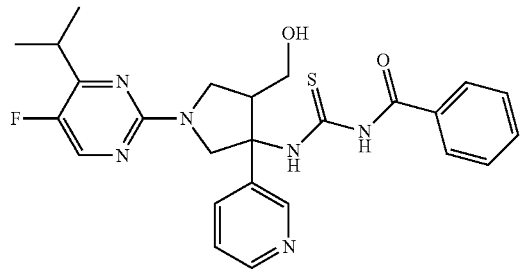 [SMILES: CC(C)c1nc(N2CC(CO)C(NC(=S)NC(=O)c3ccccc3)(c3cccnc3)C2)ncc1F] | 495 (M + 1) |
| 68 | tert-Butyl 3-(benzoylcarbamothioylamino)-4-(hydroxymethyl)-3-pyrazin-2-yl-pyrrolidine-1-carboxylate | 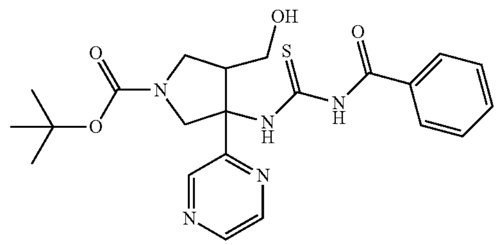 [SMILES: CC(C)(C)OC(=O)N1CC(CO)C(NC(=S)NC(=O)c2ccccc2)(c2cnccn2)C1] | 458 (M + 1) |
| 69[b] | N-[[3-(5-Fluoro-2-pyridyl)-1-(5-fluoropyrimidin-2-yl)-4-(hydroxymethyl)pyrrolidin-3-yl]carbamothioyl]benzamide | 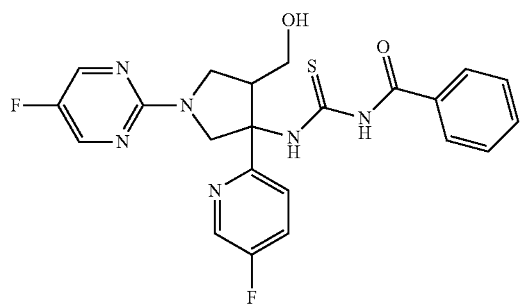 [SMILES: O=C(NC(=S)NC1(c2ccc(F)cn2)CN(c2ncc(F)cn2)CC1CO)c1ccccc1] | 471(M + 1) |
| 70[c] | tert-Butyl 3-(benzoylcarbamothioylamino)-3-(5-fluoro-2-pyridyl)-4-(hydroxymethyl)pyrrolidine-1-carboxylate | 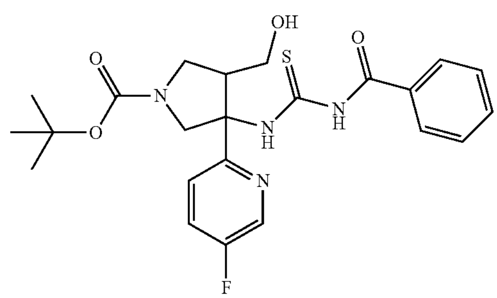 [SMILES: CC(C)(C)OC(=O)N1CC(CO)C(NC(=S)NC(=O)c2ccccc2)(c2ccc(F)cn2)C1] | 475 (M + 1) |
| 71[d] | tert-Butyl 3-(benzoylcarbamothioylamino)-4-(hydroxymethyl)-3-(3-pyridyl)pyrrolidine-1-carboxylate | 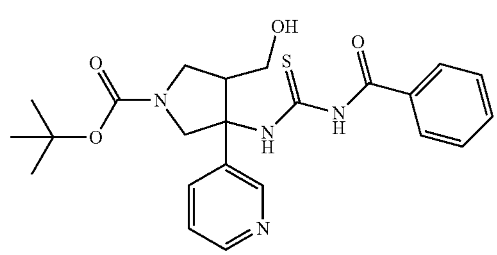 [SMILES: CC(C)(C)OC(=O)N1CC(CO)C(NC(=S)NC(=O)c2ccccc2)(c2cccnc2)C1] | 457 (M + 1) |

TABLE 13-continued

| Prep. No. | Chemical name | Structure | ES/MS (m/e) |
|---|---|---|---|
| 72[a] | N-[[1-(5-Fluoropyrimidin-2-yl)-4-(hydroxymethyl)-3-pyrazin-2-yl-pyrrolidin-3-yl]carbamothioyl]benzamide | 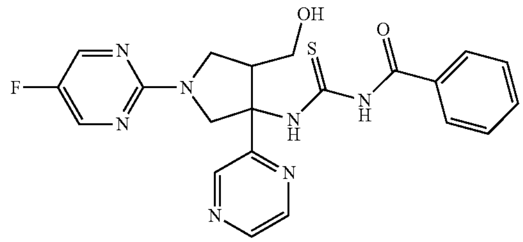 [SMILES: O=C(NC(=S)NC1(c2cnccn2)CN(c2ncc(F)cn2)CC1CO)c1ccccc1] | 454 (M + 1) |
| 73[e] | N-[[1-(5-Fluoropyrimidin-2-yl)-4-(hydroxymethyl)-3-(4-pyridyl)pyrrolidin-3-yl]carbamothioyl]benzamide | 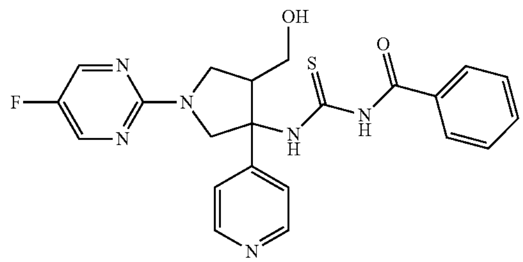 [SMILES: O=C(NC(=S)NC1(c2ccncc2)CN(c2ncc(F)cn2)CC1CO)c1ccccc1] | 453 (M + 1) |

[a]Purification conditions: silica gel column eluted a 0-10% gradient of 0.14M ammonia/methanol solution in dichloromethane.
[b]Purification conditions: silica gel column eluted with a 0-15% gradient of 2M ammonia/methanol solution in dichloromethane.
[c]Reaction is carried out at room temperature over the weekend. Product is purified by silica gel column chromatography using a 0-40% gradient of acetone in dichloromethane.
[d]Reaction is carried out at room temperature for 1 h 20 min. Product is purified by silica gel column chromatography using a 0-10% gradient of 0.14M ammonia/methanol solution in dichloromethane.
[e]Reaction is carried out at 0° C. for 1 hour, diluted with ethyl acetate, and washed with brine solution. The organic layer is dried and concentrated to give the title compound.

Preparation 74

Racemic N-[6-(5-Fluoropyrimidin-2-yl)-7a-(2-pyridyl)-4,4a,5,7-tetrahydropyrrolo[3,4-d][1,3]thiazin-2-yl]benzamide

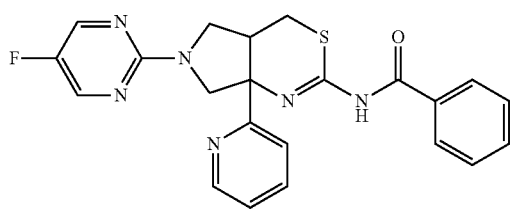 [SMILES: O=C(NC1=NC2(c3ccccn3)CN(c3ncc(F)cn3)CC2CS1)c1ccccc1]

4-Amino-1-(5-fluoropyrimidin-2-yl)-4-(2-pyridyl)pyrrolidin-3-yl]methanol (240 mg, 0.83 mmol) is dissolved in tetrahydrofuran (25 mL). The mixture is cooled to 0° C. under nitrogen and benzoyl isothiocyanate (120 mg, 0.74 mmol) is added. The resulting mixture is stirred for 30 minutes. Triphenylphosphine (260 mg, 0.981 mmol) followed by diisopropyl azodicarboxylate (340 mg, 1.68 mmol) are added and the reaction is allowed to warm to room temperature. After an hour the reaction is concentrated under reduced pressure. The resulting residue is purified by silica gel column chromatography using a 0-50% gradient of tetrahydrofuran in cyclohexane. This is further purified by achiral SFC (Supercritical Fluid Chromatography) (Column: Princeton DNP (dinitrophenyl) (5μ), 21.2×250 mm; eluent: gradient of 15-30% methanol (0.2% diethylmethylamine) in $CO_2$; flow: 65 mL/min at UV 240 nm) to give the title compound (160 mg, 44%). ES/MS (m/e): 435 (M+1).

Preparation 75

Racemic N-[6-(5-Fluoro-4-methoxy-6-methyl-pyrimidin-2-yl)-7a-pyrazin-2-yl-4,4a,5,7-tetrahydropyrrolo[3,4-d][1,3]thiazin-2-yl]benzamide

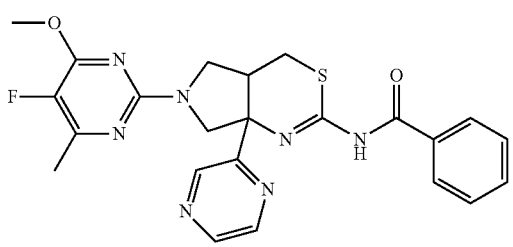 [SMILES: COc1nc(N2CC3CSC(NC(=O)c4ccccc4)=NC3(c3cnccn3)C2)nc(C)c1F]

1-Chloro-N,N,2-trimethylpropenylamine (492 μL, 3.71 mmol) is added to a stirred solution of N-[[1-(5-fluoro-4-methoxy-6-methyl-pyrimidin-2-yl)-4-(hydroxymethyl)-3-pyrazin-2-yl-pyrrolidin-3-yl]carbamothioyl]benzamide (1.32 g, 2.65 mmol) in dichloromethane (30 mL) at room temperature. The reaction mixture is stirred for 1 hour 30 minutes. Then a saturated aqueous solution of sodium bicarbonate (20 mL) is added followed by dichloromethane (70 mL). The layers are separated and the aqueous layer is re-extracted with dichloromethane (70 mL). The combined organic layers are dried over magnesium sulfate and the solvent is evaporated under reduced pressure. The resulting residue is dissolved in methanol (40 mL) and loaded on an ion exchange column. The column is eluted with methanol (60 mL) then with 7 M ammonia/methanol solution (100 mL).

The basic solvent fraction is collected and evaporated under reduced pressure. The isolated residue is further purified by silica gel column chromatography using a 0-5% gradient of 0.14 M ammonia/methanol solution in dichloromethane to give the title compound (820 mg, 64%). ES/MS (m/e): 480 (M+1).

The following compounds are prepared essentially by the method of Preparation 75.

TABLE 14

| Prep. No. | Chemical name | Structure | ES/MS (m/e) |
|---|---|---|---|
| 76 | Racemic N-[6-(5-Fluoro-4-isopropyl-pyrimidin-2-yl)-7a-pyrazin-2-yl-4,4a,5,7-tetrahydropyrrolo[3,4-d][1,3]thiazin-2-yl]benzamide | 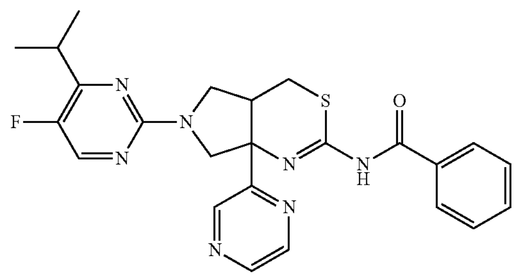 [SMILES: CC(C)c1nc(N2CC3CSC(NC(=O)c4ccccc4)=NC3(c3cnccn3)C2)ncc1F] | 478 (M + 1) |
| 77 | Racemic N-[6-(5-Fluoro-4-isopropyl-pyrimidin-2-yl)-7a-(3-pyridyl)-4,4a,5,7-tetrahydropyrrolo[3,4-d][1,3]thiazin-2-yl]benzamide | 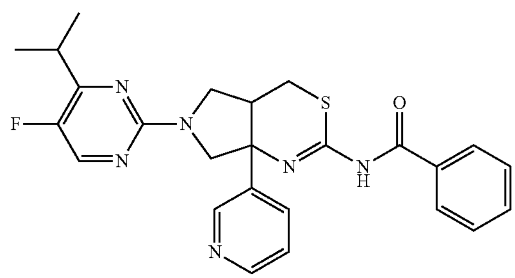 [SMILES: CC(C)c1nc(N2CC3CSC(NC(=O)c4ccccc4)=NC3(c3cccnc3)C2)ncc1F] | 477 (M +1) |
| 78[a] | Racemic N-[7a-(5-Fluoro-2-pyridyl)-6-(5-fluoropyrimidin-2-yl)-4,4a,5,7-tetrahydropyrrolo[3,4-d][1,3]thiazin-2-yl]benzamide | 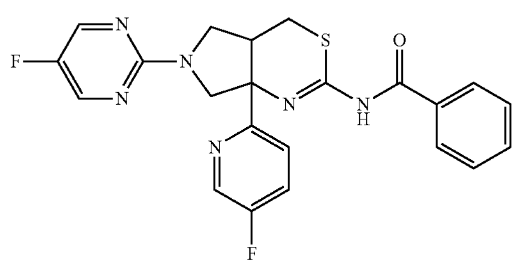 [SMILES: O=C(NC1=NC2(c3ccc(F)cn3)CN(c3ncc(F)cn3)CC2CS1)c1ccccc1] | 453 (M +1) |
| 79 | Racemic N-[6-(5-Fluoropyrimidin-2-yl)-7a-pyrazin-2-yl-4,4a,5,7-tetrahydropyrrolo[3,4-d][1,3]thiazin-2-yl]benzamide | 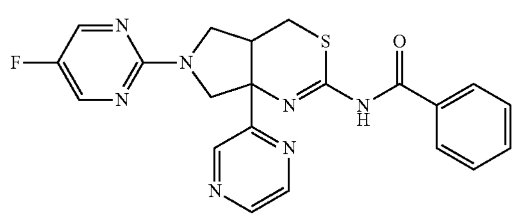 [SMILES: O=C(NC1=NC2(c3cnccn3)CN(c3ncc(F)cn3)CC2CS1)c1ccccc1] | 436 (M +1) |
| 80[b] | Racemic N-[6-(5-Fluoropyrimidin-2-yl)-7a-(4-pyridyl)-4,4a,5,7-tetrahydropyrrolo[3,4-d][1,3]thiazin-2-yl]benzamide | 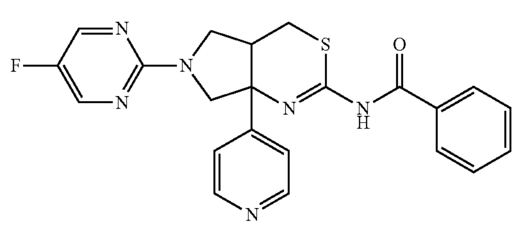 [SMILES: O=C(NC1=NC2(c3ccncc3)CN(c3ncc(F)cn3)CC2CS1)c1ccccc1] | 435 (M +1) |

[a]No ion exchange purification is used. Purification consisted of silica gel column chromatography using an isocratic run of 30% ethyl acetate in iso-hexanes followed by a gradient up to 80% of ethyl acetate in iso-hexanes to give the title compound.

[b]The reaction is carried out at 0° C. for 1 hour followed by room temperature for 16 hours. Purification is by silica gel column chromatography using a gradient of 0 to 5% 2M ammonia/methanol in chloroform to give the title compound.

Preparation 81

Racemic tert-Butyl 2-benzamido-7a-pyrazin-2-yl-4,4a,5,7-tetrahydropyrrolo[3,4-d][1,3]thiazine-6-carboxylate

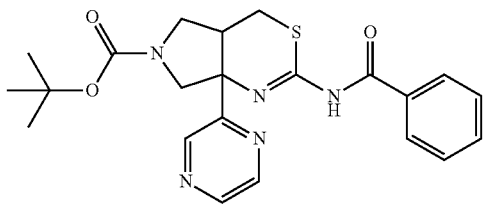 [SMILES: CC(C)(C)OC(=O)N1CC2CSC(NC(=O)c3ccccc3)=NC2(c2cnccn2)C1]

1-Chloro-N,N,2-trimethylpropenylamine (409.71 μL, 3.10 mmol) is added to a stirred solution of tert-butyl 3-(benzoylcarbamothioylamino)-4-(hydroxymethyl)-3-pyrazin-2-yl-pyrrolidine-1-carboxylate (1.09 g, 2.38 mmol) in dichloromethane (30 mL) at room temperature. After stirring the reaction at room temperature for 3 hours a saturated aqueous solution of sodium carbonate (15 mL) is added and the mixture is stirred for 5 minutes. Dichloromethane (80 mL) is added and the layers are separated. The aqueous layer is re-extracted with dichloromethane (70 mL). The combined organic layers are dried over magnesium sulfate and concentrated under reduced pressure. The isolated product is dissolved in methanol (60 mL) and is purified by ion exchange column chromatography eluting with methanol (60 mL) then with 7 M ammonia/methanol solution (120 mL). The basic fraction is collected and the resulting product is further purified by silica gel column chromatography using a 0-5% gradient of 0.14 M ammonia/methanol solution in dichloromethane to give the title product (747 mg, 71%). ES/MS (m/e) 440 (M+1).

The following compounds are prepared essentially by the method of Preparation 81.

TABLE 15

| Prep. No. | Chemical name | Structure | ES/MS (m/e) |
|---|---|---|---|
| 82[a] | Racemic tert-Butyl 2-benzamido-7a-(5-fluoro-2-pyridyl)-4,4a,5,7-tetrahydropyrrolo[3,4-d][1,3]thiazine-6-carboxylate | 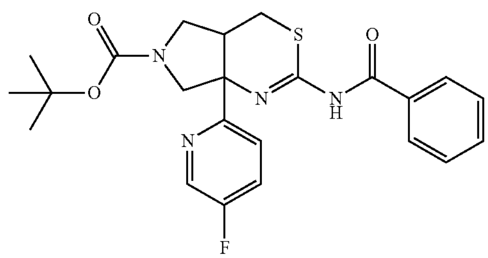 [SMILES: CC(C)(C)OC(=O)N1CC2CSC(NC(=O)c3ccccc3)=NC2(c2ccc(F)cn2)C1] | 457 (M + 1) |
| 83[b] | Racemic tert-Butyl 2-benzamido-7a-(3-pyridyl)-4,4a,5,7-tetrahydropyrrolo[3,4-d][1,3]thiazine-6-carboxylate | 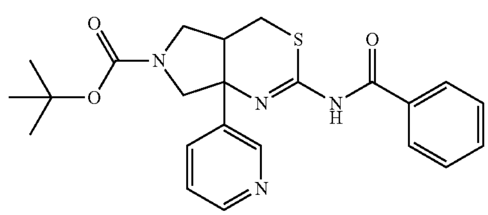 [SMILES: CC(C)(C)OC(=O)N1CC2CSC(NC(=O)c3ccccc3)=NC2(c2cccnc2)C1] | 439 (M + 1) |

[a]Reaction time is 18 hours and material is purified by silica gel column chromatography using a 0-12% gradient of acetone in dichloromethane to give the title compound.
[b]Material is purified by silica gel column chromatography using a 0-5% gradient of 0.14M ammonia/methanol solution in dichloromethane to give the title compound.

Preparation 84 tert-Butyl(4aR,7aR)-2-benzamido-7a-pyrazin-2-yl-4,4a,5,7-tetrahydropyrrolo[3,4-d][1,3]thiazine-6-carboxylate

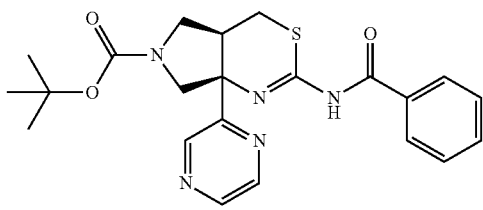 [SMILES: CC(C)(C)OC(=O)N1C[C@H]2CSC(NC(=O)c3ccccc3)=N[C@@]2(c2cnccn2)C1]

Racemic tert-butyl 2-benzamido-7a-pyrazin-2-yl-4,4a,5,7-tetrahydropyrrolo[3,4-d][1,3]thiazine-6-carboxylate is separated into its constituent enantiomers by chiral SFC (Supercritical Fluid Chromatography) (Column: Chiralpak AD-H (5µ), 30×250 mm; eluent: 50% isopropanol (0.2% diethylmethylamine) in $CO_2$; flow: 120 mL/min at UV 260 nm). The first eluting isomer is the title compound.

Preparation 85 tert-Butyl(4aR,7aR)-2-benzamido-7a-(5-fluoro-2-pyridyl)-4,4a,5,7-tetrahydropyrrolo[3,4-d][1,3]thiazine-6-carboxylate

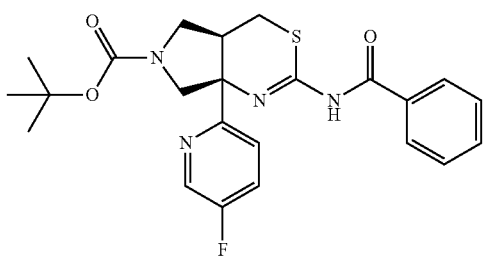 [SMILES: CC(C)(C)OC(=O)N1C[C@H]2CSC(NC(=O)c3ccccc3)=N[C@@]2(c2ccc(F)cn2)C1]

Racemic tert-butyl 2-benzamido-7a-(5-fluoro-2-pyridyl)-4,4a,5,7-tetrahydropyrrolo[3,4-d][1,3]thiazine-6-carboxylate is separated into its constituent enantiomers by chiral SFC (Column: Chiralpak AD-H (5µ), 30×250 mm; eluent: 40% methanol (0.% diethylmethylamine) in $CO_2$; flow: 120 mL/min at UV 260 nm). The second eluting isomer is the title compound.

Preparation 86 tert-Butyl(4aR,7aS)-2-benzamido-7a-(3-pyridyl)-4,4a,5,7-tetrahydropyrrolo[3,4-d][1,3]thiazine-6-carboxylate

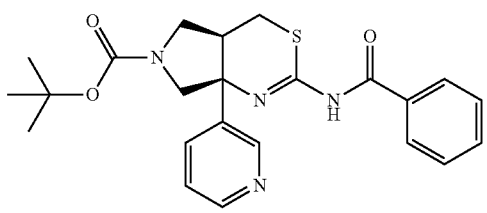 [SMILES: CC(C)(C)OC(=O)N1C[C@H]2CSC(NC(=O)c3ccccc3)=N[C@@]2(c2cccnc2)C1]

Racemic tert-butyl 2-benzamido-7a-(3-pyridyl)-4,4a,5,7-tetrahydropyrrolo[3,4-d][1,3]thiazine-6-carboxylate is separated into its constituent enantiomers by chiral SFC (Column: Chiralpak AD-H (5µ), 30×250 mm; eluent: 35% isopropanol (0.2% diethylmethylamine) in $CO_2$; flow: 130 mL/min at UV 260 nm). The first eluting isomer is the title compound.

Preparation 87

N-[(4aR,7aR)-7a-Pyrazin-2-yl-4a,5,6,7-tetrahydro-4H-pyrrolo[3,4-d][1,3]thiazin-2-yl]benzamide

Trifluoroacetic acid (1.5 mL) is added to a stirred solution of tert-butyl(4aR,7aR)-2-benzamido-7a-pyrazin-2-yl-4,4a,5,7-tetrahydropyrrolo[3,4-d][1,3]thiazine-6-carboxylate (299 mg, 0.680 mmol) in dichloromethane (6 mL) at room temperature. The reaction is stirred at room temperature for 80 minutes and the solvent is evaporated under reduced pressure. The resulting residue is dissolved in methanol (20 mL) and this solution is loaded onto an ion exchange column and eluted with methanol then with 7 M ammonia/methanol solution. The basic fraction is collected and concentrated under reduced pressure to give the title compound (231 mg, quantitative). ES/MS (m/e): 340 (M+1).

The following compounds are prepared essentially by the method of Preparation 87.

TABLE 16

| Prep. No. | Chemical name | Structure | ES/MS (m/e) |
|---|---|---|---|
| 88 | N-[(4aR,7aR)-7a-(5-Fluoro-2-pyridyl)-4a,5,6,7-tetrahydro-4H-pyrrolo[3,4-d][1,3]thiazin-2-yl]benzamide | 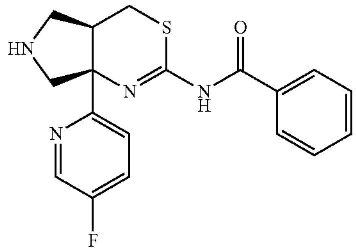 [SMILES: O=C(NC1=N[C@@]2(c3ccc(F)cn3)CNC[C@H]2CS1)c1ccccc1] | 357 (M +1) |
| 89 | N-[(4aR,7aS)-7a-(3-Pyridyl-4a,5,6,7-tetrahydro-4H-pyrrolo[3,4-d][1,3]thiazin-2-yl]benzamide | 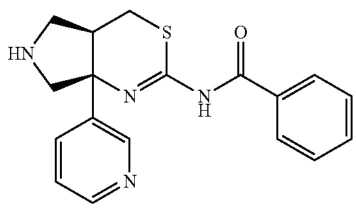 [SMILES: O=C(NC1=N[C@@]2(c3cccnc3)CNC[C@H]2CS1)c1ccccc1] | 339 (M +1) |

Preparation 90

N-[(4aR,7aR)-6-[5-Fluoro-4-(1-hydroxy-1-methyl-ethyl)pyrimidin-2-yl]-7a-pyrazin-2-yl-4,4a,5,7-tetrahydropyrrolo[3,4-d][1,3]thiazin-2-yl]benzamide

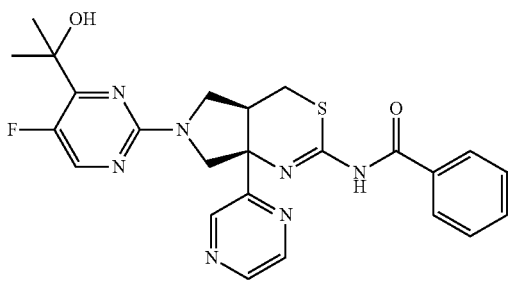 [SMILES: CC(C)(O)c1nc(N2C[C@H]3CSC(NC(=O)c4ccccc4)=N[C@@]3(c3cnccn3)C2)ncc1F]

N-[(4aR,7aR)-7a-pyrazin-2-yl-4a,5,6,7-tetrahydro-4H-pyrrolo[3,4-d][1,3]thiazin-2-yl]benzamide (231 mg, 0.680 mmol) is dissolved in 1,4-dioxane (4 mL). 2-(2-Chloro-5-fluoro-pyrimidin-4-yl)propan-2-ol (648.60 mg, 3.40 mmol) and diisopropylethylamine (653 μL, 3.74 mmol) are added. The reaction is heated at 110° C. for 6 hours then cooled to room temperature and concentrated under reduced pressure. The resulting residue is purified by silica gel column chromatography using a 0-5% gradient of 0.14 M ammonia/methanol solution in dichloromethane to give the title compound (330 mg, 98%). ES/MS (m/e): 494 (M+1).

The following compounds are prepared essentially by the method of Preparation 90

TABLE 17

| Prep. No. | Chemical name | Structure | ES/MS (m/e) |
|---|---|---|---|
| 91 | N-[(4aR,7aR)-6-[5-Fluoro-4-(1-fluoro-1-methyl-ethyl)pyrimidin-2-yl]-7a-pyrazin-2-yl-4,4a,5,7-tetrahydropyrrolo[3,4-d][1,3]thiazin-2-yl]benzamide | 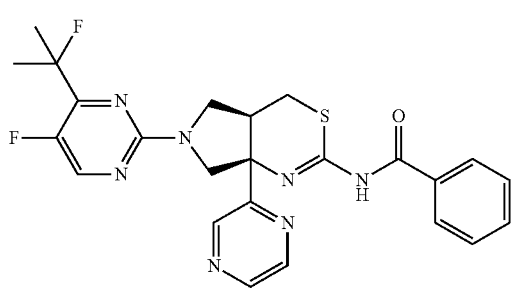 [SMILES: CC(C)(F)c1nc(N2C[C@H]3CSC(NC(=O)c4ccccc4)=N[C@@]3(c3cnccn3)C2)ncc1F] | 496 (m + 1) |

TABLE 17-continued

| Prep. No. | Chemical name | Structure | ES/MS (m/e) |
|---|---|---|---|
| 92[a] | N-[(4aR,7aR)-6-(4-Ethyl-5-fluoro-pyrimidin-2-yl)-7a-pyrazin-2-yl-4,4a,5,7-tetrahydropyrrolo[3,4-d][1,3]thiazin-2-yl]benzamide | 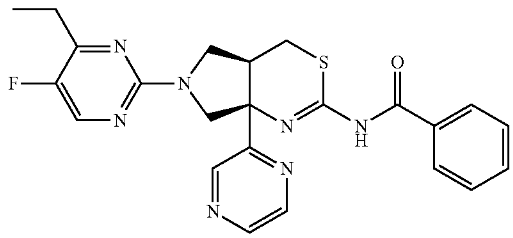 [SMILES: CCc1nc(N2C[C@H]3CSC(NC(=O)c4ccccc4)=N[C@@]3(c3cnccn3)C2)ncc1F] | 464 (M + 1) |
| 93[b] | N-[(4aR,7aR)-6-[5-Fluoro-4-(1-hydroxy-1-methyl-ethyl)pyrimidin-2-yl]-7a-(5-fluoro-2-pyridyl)-4,4a,5,7-tetrahydropyrrolo[3,4-d][1,3]thiazin-2-yl]benzamide | 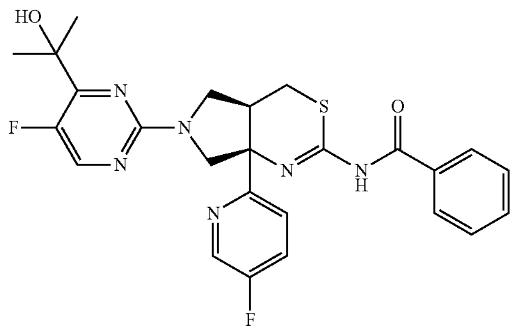 | 511 (M + 1) |
| 94[c] | N-[(4aR,7aR)-6-[5-Fluoro-4-(1-fluoro-1-methyl-ethyl)pyrimidin-2-yl]-7a-(5-fluoro-2-pyridyl)-4,4a,5,7-tetrahydropyrrolo[3,4-d][1,3]thiazin-2-yl]benzamide | 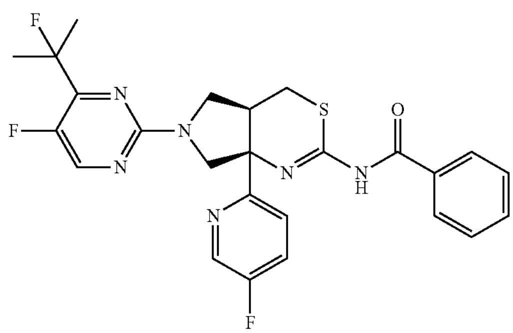 [SMILES: CC(C)(F)c1nc(N2C[C@H]3CSC(NC(=O)c4ccccc4)=N[C@@]3(c3ccc(F)cn3)C2)ncc1F] | 513 (M +1) |
| 95 | N-[(4aR,7aR)-6-(5-Fluoro-4,6-dimethoxy-pyrimidin-2-yl)-7a-(5-fluoro-2-pyridyl)-4,4a,5,7-tetrahydropyrrolo[3,4-d][1,3]thiazin-2-yl]benzamide | 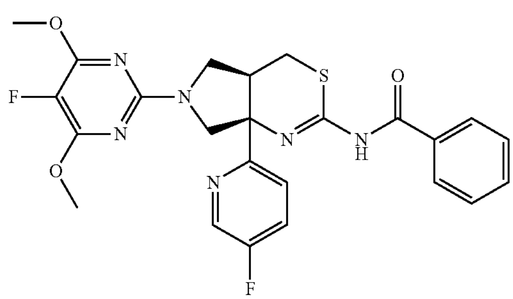 [SMILES: COc1nc(N2C[C@H]3CSC(NC(=O)c4ccccc4)=N[C@@]3(c3ccc(F)cn3)C2)nc(OC)c1F] | 513 (M + 1) |
| 96 | N-[(4aR,7aS)-6-[5-Fluoro-4-(1-hydroxy-1-methyl-ethyl)pyrimidin-2-yl]-7a-(3-pyridyl)-4,4a,5,7-tetrahydropyrrolo[3,4-d][1,3]thiazin-2-yl]benzamide | 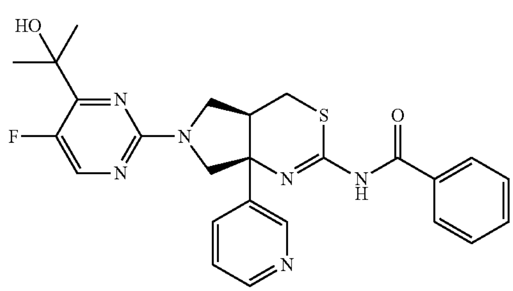 | 493 (M + 1) |

TABLE 17-continued

| Prep. No. | Chemical name | Structure | ES/MS (m/e) |
|---|---|---|---|
| 97 | N-[(4aR,7aS)-6-[5-Fluoro-4-(1-fluoro-1-methyl-ethyl)pyrimidin-2-yl]-7a-(3-pyridyl)-4,4a,5,7-tetrahydropyrrolo[3,4-d][1,3]thiazin-2-yl]benzamide | 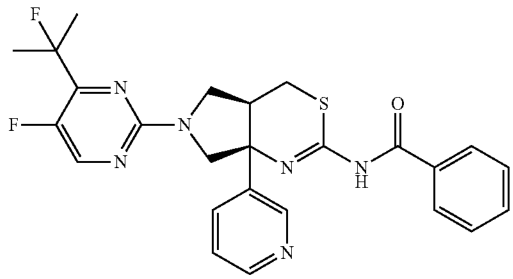 [SMILES: CC(C)(F)c1nc(N2C[C@H]3CSC(NC(=O)c4ccccc4)=N[C@@]3(c3cccnc3)C2)ncc1F] | 495 (M +1) |
| 98[e] | N-[(4aR,7aS)-6-(5-Fluoro-4-methoxy-6-methyl-pyrimidin-2-yl)-7a-(3-pyridyl)-4,4a,5,7-tetrahydropyrrolo[3,4-d][1,3]thiazin-2-yl]benzamide | 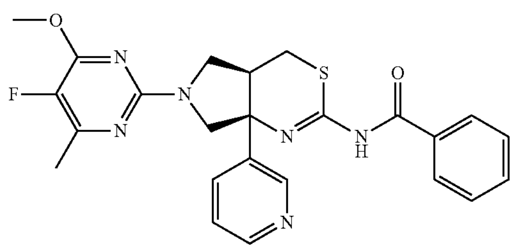 [SMILES: COc1nc(N2C[C@H]3CSC(NC(=O)c4ccccc4)=N[C@@]3(c3cccnc3)C2)nc(C)c1F] | 479 (M + 1) |

[a] The reaction is heated for 8 hours.
[b] The reaction is heated for 1 hour 30 minutes. Product is purified by silica gel column chromatography using a 0-20% methanol in dichloromethane gradient.
[c] The reaction is heated overnight. The product is purified by silica gel column chromatography using a 0-20% methanol in dichloromethane gradient.
[d] The reaction is heated at 110° C. for 23 hours. It is purified by silica gel column chromatography using a 0-20% gradient of methanol in dichloromethane.
[e] The reaction is heated at 110° C. overnight. It is purified by silica gel column chromatography using a 0-10% gradient of methanol in dichloromethane.

Example A

2-[2-[(4aR,7aR)-2-Amino-7a-pyrazin-2-yl-4,4a,5,7-tetrahydropyrrolo[3,4-d][1,3]thiazin-6-yl]-5-fluoro-pyrimidin-4-yl]propan-2-ol

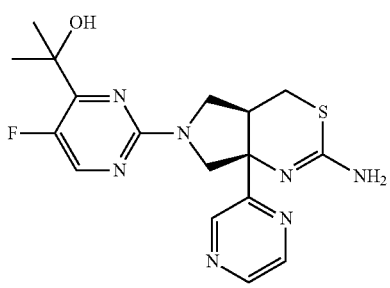 [SMILES: CC(C)(O)c1nc(N2C[C@H]3CSC(N)=N[C@@]3(c3cnccn3)C2)ncc1F]

N-[(4aR,7aR)-6-[5-fluoro-4-(1-hydroxy-1-methyl-ethyl)pyrimidin-2-yl]-7a-pyrazin-2-yl-4,4a,5,7-tetrahydropyrrolo[3,4-d][1,3]thiazin-2-yl]benzamide (330 mg, 0.668 mmol) is dissolved in methanol (8 mL) with stirring. Lithium hydroxide (42.51 mg, 1 mmol) is added and the reaction is heated at 60° C. for 5 hours 30 minutes. The reaction is cooled to room temperature and loaded onto a silica gel column. The column is eluted with a 0-5% gradient of 0.14 M ammonia/methanol in dichloromethane. The product obtained is further purified by preparative HPLC using a 10% B to 100% B gradient over 9 minutes at 60 mL/minute (column=Phenomenex Gemini NX C18, 30×100 mm, 5 μm. Mobile phase A: water with 10 mM ammonium bicarbonate, pH adjusted to pH 10 with ammonia. Mobile phase B: acetonitrile) to give the title compound (146 mg, 56%). ES/MS (m/e): 390 (M+1).

The following compounds are prepared essentially by the method of Example A.

TABLE 18

| Ex. No. | Chemical name | Structure | ES/MS (m/e) |
|---|---|---|---|
| B | (4aR,7aR)-6-[5-Fluoro-4-(1-fluoro-1-methyl-ethyl)pyrimidin-2-yl]-7a-pyrazin-2-yl-4,4a,5,7-tetrahydropyrrolo[3,4-d][1,3]thiazin-2-amine | 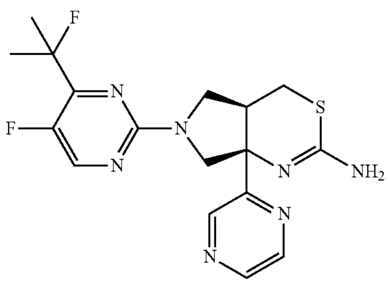 [SMILES: CC(C)(F)c1nc(N2C[C@H]3CSC(N)=N[C@@]3(c3cnccn3)C2)ncc1F] | 392 (M + 1) |
| C | (4aR,7aR)-6-(4-Ethyl-5-fluoro-pyrimidin-2-yl)-7a-pyrazin-2-yl-4,4a,5,7-tetrahydropyrrolo[3,4-d][1,3]thiazin-2-amine | 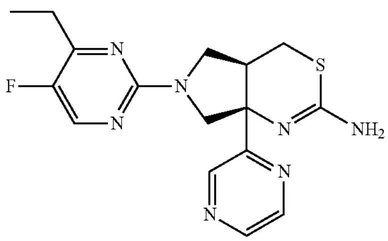 [SMILES: CCc1nc(N2C[C@H]3CSC(N)=N[C@@]3(c3cnccn3)C2)ncc1F] | 360 (M + 1) |
| D[a] | 2-[2-[(4aR,7aR)-2-Amino-7a-(5-fluoro-2-pyridyl-4,4a,5,7-tetrahydropyrrolo[3,4-d][1,3]thiazin-6-yl]-5-fluoro-pyrimidin-4-yl]propan-2-ol | 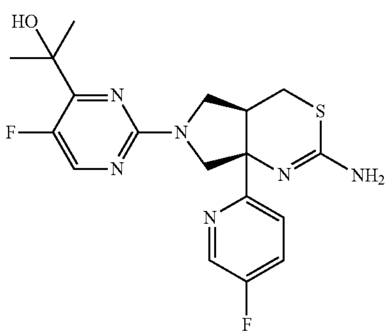 [SMILES: CC(C)(O)c1nc(N2C[C@H]3CSC(N)=N[C@@]3(c3ccc(F)cn3)C2)ncc1F] | 407 (M + 1) |
| E[b] | (4aR,7aR)-6-[5-Fluoro-4-(1-fluoro-1-methyl-ethyl)pyrimidin-2-yl]-7a-(5-fluoro-2-pyridyl)-4,4a,5,7-tetrahydropyrrolo[3,4-d][1,3]thiazin-2-amine | 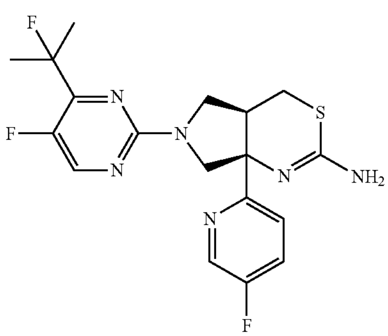 [SMILES: CC(C)(F)c1nc(N2C[C@H]3CSC(N)=N[C@@]3(c3ccc(F)cn3)C2)ncc1F] | 409 (M +1) |
| F[a] | (4aR,7aR)-6-(5-Fluoro-4,6-dimethoxy-pyrimidin-2-yl)-7a-(5-fluoro-2-pyridyl)-4,4a,5,7-tetrahydropyrrolo[3,4-d][1,3]thiazin-2-amine | 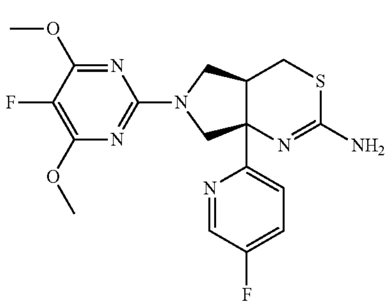 [SMILES: COc1nc(N2C[C@H]3CSC(N)=N[C@@]3(c3ccc(F)cn3)C2)nc(OC)c1F] | 409 (M + 1) |

TABLE 18-continued

| Ex. No. | Chemical name | Structure | ES/MS (m/e) |
|---|---|---|---|
| G | 2-[2-[(4aR,7aS)-2-Amino-7a-(3-pyridyl)-4,4a,5,7-tetrahydropyrrolo[3,4-d][1,3]thiazin-6-yl]-5-fluoro-pyrimidin-4-yl]propan-2-ol | 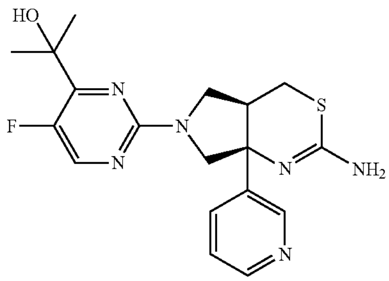 | 389 (M + 1) |
| H | (4aR,7aS)-6-[5-Fluoro-4-(1-fluoro-1-methyl-ethyl)pyrimidin-2-yl]-7a-(3-pyridyl)-4,4a,5,7-tetrahydropyrrolo[3,4-d][1,3]thiazin-2-amine | 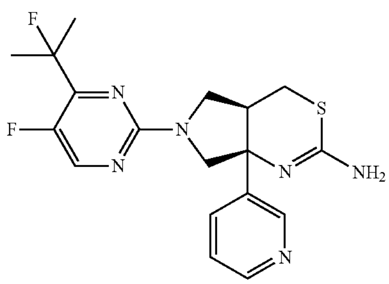 [SMILES: CC(C)(F)c1nc(N2C[C@H]3CSC(N)=N[C@@]3(c3cccnc3)C2)ncc1F] | 391 (M + 1) |
| I | (4aR,7aS)-6-(5-Fluoro-4-methoxy-6-methyl-pyrimidin-2-yl)-7a-(3-pyridyl)-4,4a,5,7-tetrahydropyrrolo[3,4-d][1,3]thiazin-2-amine | 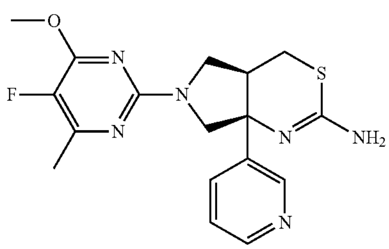 [SMILES: COc1nc(N2C[C@H]3CSC(N)=N[C@@]3(c3cccnc3)C2)nc(C)c1F] | 375 (M + 1) |

<sup>a</sup>Purification is by preparative LCMS using a 10% B to 100% B gradient at 45 mL/minute (column = X-Bridge C18, 30 ×100 mm, 5μ. Mobile phase A: water with 10 mM ammonium bicarbonate, pH adjusted to pH 10 with ammonia. Mobile phase B: 50/50 methanol/acetonitrile).
<sup>b</sup>Purification is by silica gel column chromatography using a 0-20% gradient of 2M NH₃ in methanol solution in dichloromethane

Example J

Racemic 6-(5-Fluoropyrimidin-2-yl)-7a-(3-pyridyl)-4,4a,5,7-tetrahydropyrrolo[3,4-d][1,3]thiazin-2-amine

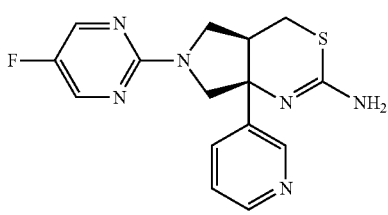 [SMILES: NC1=N[C@@]2(c3cccnc3)CN(c3ncc(F)cn3)C[C@H]2CS1]

To a stirred solution of N-[6-(5-fluoropyrimidin-2-yl)-7a-(3-pyridyl)-4,4a,5,7-tetrahydropyrrolo[3,4-d][1,3]thiazin-2-yl]benzamide (110 mg, 0.210 mmol) in ethanol (10 mL) are added pyridine (187 μL 2.31 mmol) and O-methylhydroxylamine hydrochloride (143 mg, 1.68 mmol). The mixture is heated at 70° C. with stirring for 17 hours. The solvent is removed under reduced pressure. The residue is purified by silica gel chromatography using a 0-10% gradient of 0.14 M ammonia/methanol solution in dichloromethane to give the title compound (62 mg, 89%). ES/MS (m/e): 331 (M+1).

The following Examples are prepared essentially by the method of Example J with reaction times varying from 2-18 hr and temperature varying from 65-80° C.

TABLE 19

| Ex. No. | Chemical name | Structure | ES/MS (m/e) |
|---|---|---|---|
| K | Racemic 6-(5-Fluoro-4-isopropyl-pyrimidin-2-yl)-7a-(3-pyridyl)-4,4a,5,7-tetrahydropyrrolo[3,4-d][1,3]thiazin-2-amine | 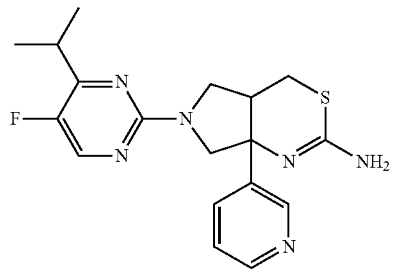 [SMILES: CC(C)c1nc(N2CC3CSC(N)=NC3(c3cccnc3)C2)ncc1F] | 373 (M + 1) |
| L | Racemic 6-(5-Fluoro-4-isopropyl-pyrimidin-2-yl)-7a-pyrazin-2-yl-4,4a,5,7-tetrahydropyrrolo[3,4-d][1,3]thiazin-2-amine | 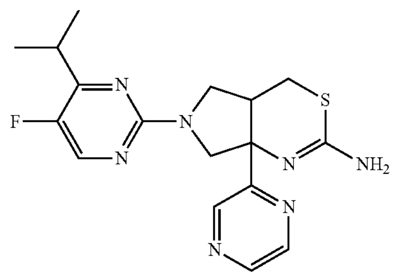 [SMILES: CC(C)c1nc(N2CC3CSC(N)=NC3(c3cnccn3)C2)ncc1F] | 374 (M + 1) |
| M | Racemic 6-(5-Fluoro-4-methoxy-6-methyl-pyrimidin-2-yl)-7a-pyrazin-2-yl-4,4a,5,7-tetrahydropyrrolo[3,4-d][1,3]thiazin-2-amine | 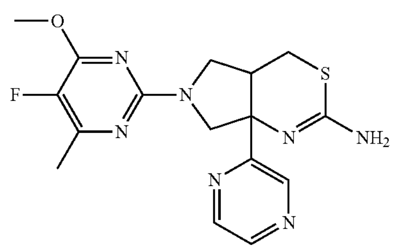 [SMILES: COc1nc(N2CC3CSC(N)=NC3(c3cnccn3)C2)nc(C)c1F] | 376 (M + 1) |
| N | Racemic 6-(5-Fluoropyrimidin-2-yl)-7a-(2-pyridyl)-4,4a,5,7-tetrahydropyrrolo[3,4-d][1,3]thiazin-2-amine | 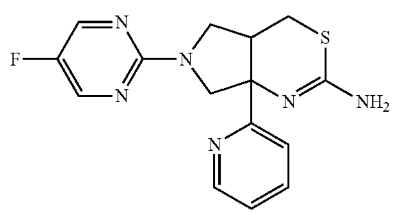 [SMILES: NC1=NC2(c3ccccn3)CN(c3ncc(F)cn3)CC2CS1] | 331 (M + 1) |
| O | Racemic 7a-(5-Fluoro-2-pyridyl)-6-(5-fluoropyrimidin-2-yl)-4,4a,5,7-tetrahydropyrrolo[3,4-d][1,3]thiazin-2-amine | 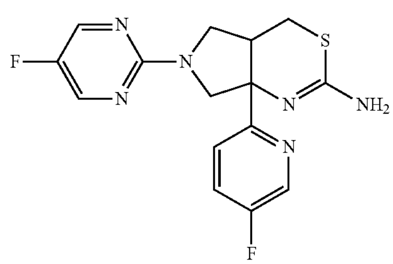 [SMILES: NC1=NC2(c3ccc(F)cn3)CN(c3ncc(F)cn3)CC2CS1] | 349 (M + 1) |
| P | Racemic 6-(5-Fluoropyrimidin-2-yl)-7a-pyrazin-2-yl-4,4a,5,7-tetrahydropyrrolo[3,4-d][1,3]thiazin-2-amine | 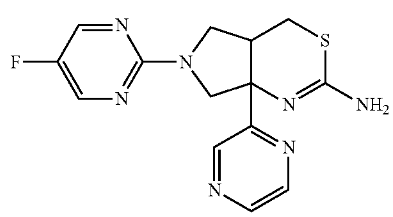 | 332 (M + 1) |

TABLE 19-continued

| Ex. No. | Chemical name | Structure | ES/MS (m/e) |
|---|---|---|---|
| Q[a] | Racemic 6-(5-Fluoropyrimidin-2-yl)-7a-(4-pyridyl)-4,4a,5,7-tetrahydropyrrolo[3,4-d][1,3]thiazin-2-amine | 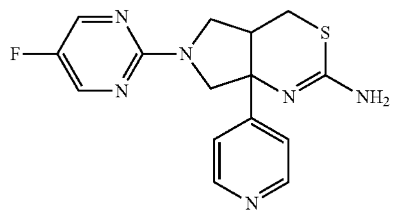 [SMILES: NC1=NC2(c3ccncc3)CN(c3ncc(F)cn3)CC2CS1] | 331 (M + 1) |

[a]Purification is by silica gel column chromatography using a gradient of 0 to 10% 2M ammonia/methanol in chloroform to give the title compound

Example R (4aR,7aR)-6-(5-Fluoro-4-methoxy-6-methyl-pyrimidin-2-yl)-7a-pyrazin-2-yl-4,4a,5,7-tetrahydropyrrolo[3,4-d][1,3]thiazin-2-amine

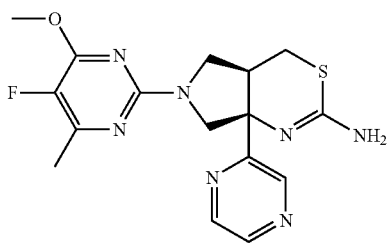

Racemic 6-(5-fluoro-4-methoxy-6-methyl-pyrimidin-2-yl)-7a-pyrazin-2-yl-4,4a,5,7-tetrahydropyrrolo[3,4-d][1,3]thiazin-2-amine (490 mg, 1.3 mmol) is separated into its constituent enantiomers by chiral SFC (Column: Chiralcel OD-H (5µ), 21.2×250 mm; eluent: 50% methanol (0.2% diethylmethylamine) in CO$_2$; flow: 70 mL/min at UV 260 nm). The first eluting isomer is the title compound (206 mg, 32%). ES/MS (m/e): 376 (M+1).

Example 1

(4aR,7aS)-6-(5-Fluoropyrimidin-2-yl)-7a-(3-pyridyl)-4,4a,5,7-tetrahydropyrrolo[3,4-d][1,3]thiazin-2-amine

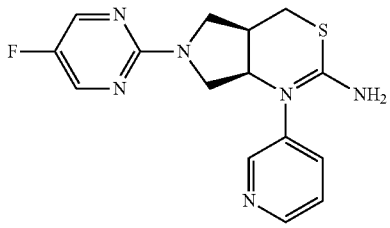

Racemic 6-(5-fluoropyrimidin-2-yl)-7a-(3-pyridyl)-4,4a,5,7-tetrahydropyrrolo[3,4-d][1,3]thiazin-2-amine (137 mg, 0.415 mmol) is separated into its constituent enantiomers by chiral SFC (Column: Chiralpak AD-H (5µ), 21.2×250 mm; eluent: 35% isopropanol (0.2% diethylmethylamine) in CO$_2$; flow: 70 mL/min at UV 260 nm). The second eluting isomer is the title compound (19 mg). ES/MS (m/e): 331 (M+1).

Example 2

(4aR,7aS)-6-(5-Fluoro-4-isopropyl-pyrimidin-2-yl)-7a-(3-pyridyl)-4,4a,5,7-tetrahydropyrrolo[3,4-d][1,3]thiazin-2-amine

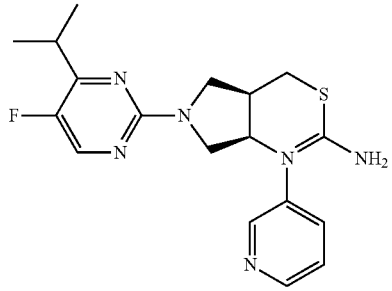

Racemic 6-(5-fluoro-4-isopropyl-pyrimidin-2-yl)-7a-(3-pyridyl)-4,4a,5,7-tetrahydropyrrolo[3,4-d][1,3]thiazin-2-amine (210 mg, 0.564 mmol) is separated into its constituent enantiomers by chiral SFC (Column: Chiralcel OD-H (5µ), 21.2×250 mm; eluent: 25% methanol (0.2% diethylmethylamine) in CO$_2$; flow: 70 mL/min at UV 260 nm). The first eluting isomer is further purified again by chiral SFC (Column: Chiralcel OD-H (5µ), 21.2×250 mm; eluent: 15% methanol (0.2% diethylmethylamine) in CO$_2$; flow: 70 mL/min at UV 260 nm) to obtain the title compound (71 mg). ES/MS (m/e): 373 (M+1).

Example 3

(4aR,7aR)-6-(5-Fluoro-4-isopropyl-pyrimidin-2-yl)-7a-pyrazin-2-yl-4,4a,5,7-tetrahydropyrrolo[3,4-d][1,3]thiazin-2-amine, isomer 1

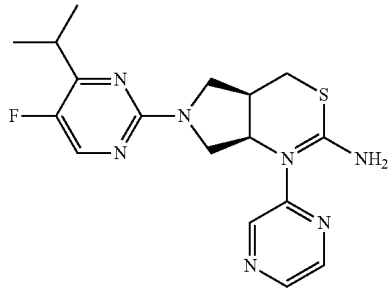

Racemic 6-(5-fluoro-4-isopropyl-pyrimidin-2-yl)-7a-pyrazin-2-yl-4,4a,5,7-tetrahydropyrrolo[3,4-d][1,3]thiazin-2-amine (127 mg, 0.340 mmol) is separated into its constituent enantiomers by chiral SFC (Column: Chiralcel OD-H (5μ), 21.2×250 mm; eluent: 50% ethanol (0.2% diethylmethylamine) in CO$_2$; flow: 70 mL/min at UV 260 nm). The first eluting isomer is the title compound (54 mg). ES/MS (m/e): 374 (M+1).

Example 4

(4aR,7aR)-6-(5-Fluoropyrimidin-2-yl)-7a-(2-pyridyl)-4,4a,5,7-tetrahydropyrrolo[3,4-d][1,3]thiazin-2-amine

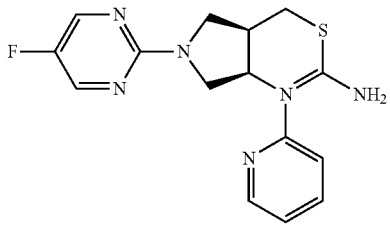

Racemic 6-(5-fluoropyrimidin-2-yl)-7a-(2-pyridyl)-4,4a,5,7-tetrahydropyrrolo[3,4-d][1,3]thiazin-2-amine (82 mg) is separated into its constituent enantiomers by chiral SFC (Column: Chiralpak IC (5μ), 30×250 mm; eluent: 55% isopropanol (0.4% diethylmethylamine) in CO$_2$; flow: 70 mL/min at UV 240 nm). The first eluting isomer is the title compound (37.7 mg). ES/MS (m/e): 331 (M+1).

Example 5

(4aR,7aR)-7a-(5-Fluoro-2-pyridyl)-6-(5-fluoropyrimidin-2-yl)-4,4a,5,7-tetrahydropyrrolo[3,4-d][1,3]thiazin-2-amine, isomer-2

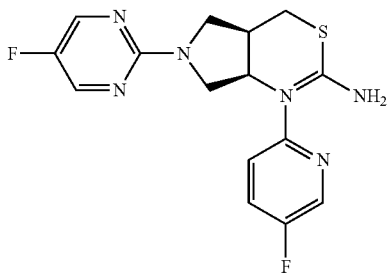

Racemic 7a-(5-fluoro-2-pyridyl)-6-(5-fluoropyrimidin-2-yl)-4,4a,5,7-tetrahydropyrrolo[3,4-d][1,3]thiazin-2-amine (60 mg, 0.172 mmol) is separated into its constituent enantiomers by chiral SFC (Column: Chiralpak AD-H (5μ), 21.2×250 mm; eluent: 40% ethanol (0.2% diethylmethylamine) in CO$_2$; flow: 70 mL/min at UV 260 nm). The second eluting isomer is the title compound (23.8 mg). ES/MS (m/e): 349 (M+1).

Example 6

(4aR,7aS)-6-(5-Fluoropyrimidin-2-yl)-7a-(4-pyridyl)-4,4a,5,7-tetrahydropyrrolo[3,4-d][1,3]thiazin-2-amine, isomer-2

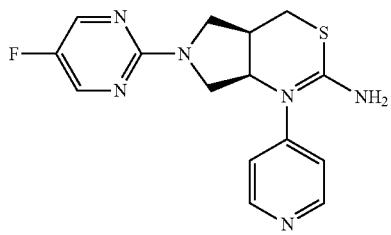

Racemic 6-(5-fluoropyrimidin-2-yl)-7a-(4-pyridyl)-4,4a,5,7-tetrahydropyrrolo[3,4-d][1,3]thiazin-2-amine (185 mg, 0.56 mmol) is separated into its constituent enantiomers by chiral SFC (Column: Chiralcel OJ-H (5μ), 21.2×250 mm; eluent: 25% ethanol (0.2% diethylmethylamine) in CO$_2$; flow: 70 mL/min at UV 260 nm). The second eluting isomer is the title compound (40 mg). ES/MS (m/e): 331 (M+1).

Example 7

(4aR,7aR)-6-(5-Fluoropyrimidin-2-yl)-7a-pyrazin-2-yl-4,4a,5,7-tetrahydropyrrolo[3,4-d][1,3]thiazin-2-amine, isomer 1

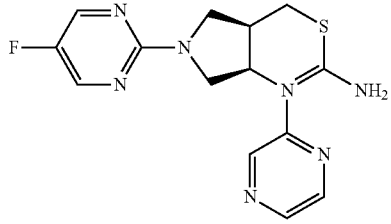

Racemic 6-(5-fluoropyrimidin-2-yl)-7a-pyrazin-2-yl-4,4a,5,7-tetrahydropyrrolo[3,4-d][1,3]thiazin-2-amine (520 mg, 1.57 mmol) is separated into its constituent enantiomers by chiral SFC (Column: Chiralcel OD-H (5μ), 21.2×250 mm; eluent: 45% methanol (0.2% diethylmethylamine) in CO$_2$; flow: 70 mL/min at UV 260 nm). The first eluting isomer is the title compound (230 mg). ES/MS (m/e): 332 (M+1).

Example 8

2-[2-[(4aR,7aR)-2-Amino-7a-pyrazin-2-yl-4,4a,5,7-tetrahydropyrrolo[3,4-d][1,3]thiazin-6-yl]-5-fluoro-pyrimidin-4-yl]propan-2-ol hydrochloride

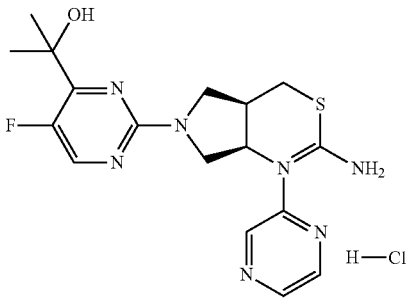

2-[2-[(4aR,7aR)-2-amino-7a-pyrazin-2-yl-4,4a,5,7-tetrahydropyrrolo[3,4-d][1,3]thiazin-6-yl]-5-fluoro-pyrimidin-4-yl]propan-2-ol (120 mg, 0.308 mmol) is dissolved in 0.1 M HCl (3.1 mL) and acetonitrile (1 mL). The resulting solution is freeze dried to obtain the title compound as a white solid. ES/MS (m/e): 390 (M+1).

The following compounds are prepared essentially by the method of Example 8.

TABLE 20

| Ex. No. | Chemical name | Structure | ES/MS (m/e) |
| --- | --- | --- | --- |
| 9 | (4aR,7aR)-6-[5-Fluoro-4-(1-fluoro-1-methyl-ethyl)pyrimidin-2-yl]-7a-pyrazin-2-yl-4,4a,5,7-tetrahydropyrrolo[3,4-d][1,3]thiazin-2-amine hydrochloride | 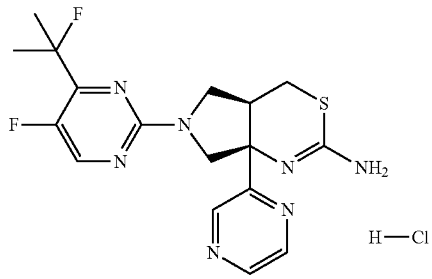 [SMILES: CC(C)(F)c1nc(N2C[C@H]3CSC(N)=N[C@@]3(c3cnccn3)C2)ncc1F ; Cl] | 392 (M + 1) |
| 10 | (4aR,7aR)-6-(4-ethyl-5-Fluoro-pyrimidin-2-yl)-7a pyrazin-2-yl-4,4a,5,7-tetrahydropyrrolo[3,4-d][1,3]thiazin-2-amine hydrochloride | 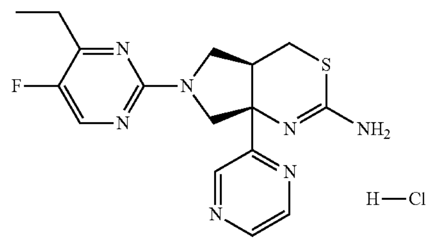 [SMILES: CCc1nc(N2C[C@H]3CSC(N)=N[C@@]3(c3cnccn3)C2)ncc1F ; Cl] | 360 (M + 1) |
| 11 | (4aR,7aR)-6-(5-Fluoro-4-methoxy-6-methyl-pyrimidin-2-yl)-7a-pyrazin-2-yl-4,4a,5,7-tetrahydropyrrolo[3,4-d][1,3]thiazin-2-amine hydrochloride | 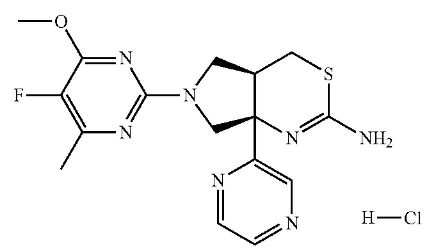 [SMILES: COc1nc(N2C[C@H]3CSC(N)=N[C@@]3(c3cnccn3)C2)nc(C)c1F ; Cl] | 376 (M + 1) |
| 12 | 2-[2-[(4aR,7aR)-2-Amino-7a-(5-fluoro-2-pyridyl)-4,4a,5,7-tetrahydropyrrolo[3,4-d][1,3]thiazin-6-yl]-5-fluoro-pyrimidin-4-yl]propan-2-ol hydrochloride | 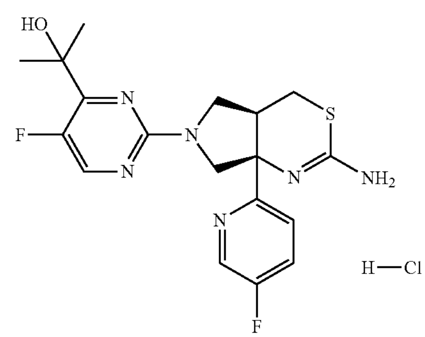 [SMILES: CC(C)(O)c1nc(N2C[C@H]3CSC(N)=N[C@@]3(c3ccc(F)cn3)C2)ncc1F ; Cl] | 407 (M + 1) |
| 13 | ((4aR,7aR)-6-[5-Fluoro-4-(1-fluoro-1-methyl-ethyl)pyrimidin-2-yl]-7a-(5-fluoro-2-pyridyl)-4,4a,5,7-tetrahydropyrrolo[3,4-d][1,3]thiazin-2-amine hydrochloride | 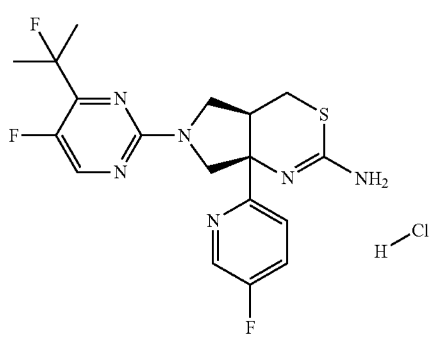 [SMILES: CC(C)(F)c1nc(N2C[C@H]3CSC(N)=N[C@@]3(c3ccc(F)cn3)C2)ncc1F ; Cl] | 409 (M + 1) |

TABLE 20-continued

| Ex. No. | Chemical name | Structure | ES/MS (m/e) |
|---|---|---|---|
| 14 | (4aR,7aR)-6-(5-Fluoro-4,6-dimethoxy-pyrimidin-2-yl)-7a-(5-fluoro-2-pyridyl)-4,4a,5,7-tetrahydropyrrolo[3,4-d][1,3]thiazin-2-amine hydrochloride | 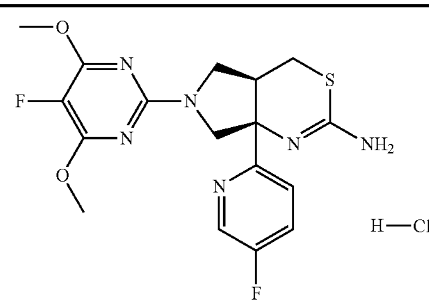 | 409 (M + 1) |
| 15 | 2-[2-[(4aR,7aS)-2-Amino-7a-(3-pyridyl)-4,4a,5,7-tetrahydropyrrolo[3,4-d][1,3]thiazin-6-yl]-5-fluoro-pyrimidin-4-yl]propan-2-ol hydrochloride | 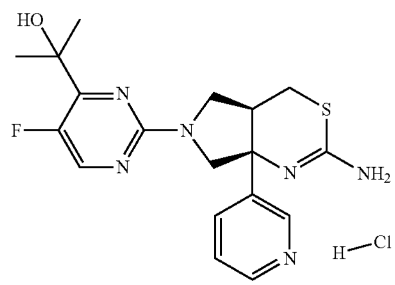 | 389 (M + 1) |
| 16 | (4aR,7aS)-6-[5-Fluoro-4-(1-fluoro-1-methyl-ethyl)pyrimidin-2-yl]-7a-(3-pyridyl)-4,4a,5,7-tetrahydropyrrolo[3,4-d][1,3]thiazin-2-amine hydrochloride | 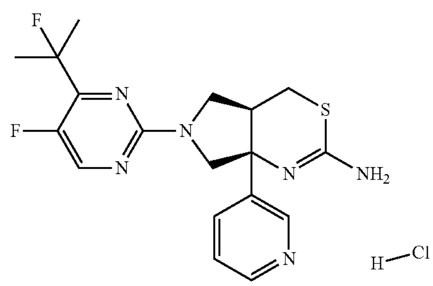 [SMILES: CC(C)(F)c1nc(N2C[C@H]3CSC(N)=N[C@@]3(c3cccnc3)C2)ncc1F ; Cl] | 391 (M + 1) |
| 17 | (4aR,7aS)-6-(5-Fluoro-4-methoxy-6-methyl-pyrimidin-2-yl)-7a-(3-pyridyl)-4,4a,5,7-tetrahydropyrrolo[3,4-d][1,3]thiazin-2-amine hydrochloride | 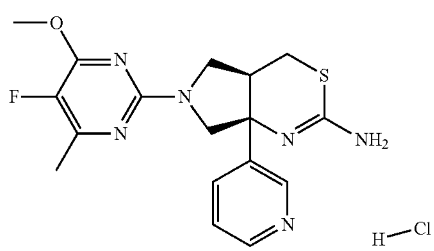 [SMILES: COc1nc(N2C[C@H]3CSC(N)=N[C@@]3(c3cccnc3)C2)nc(C)c1F ; Cl] | 375 (M + 1) |

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 1 nM in a 96-well round-bottom plate before conducting the in vitro enzymatic and whole cell assays.

Preparation of Recombinant Human BACE1

Human BACE1 (accession number: AF190725) is cloned from total brain cDNA by room temperature-PCR. The nucleotide sequences corresponding to amino acid sequences #1 to 460 are inserted into the cDNA encoding human IgG$_1$(Fc) polypeptide (Vassar et al. 1999). This fusion protein of BACE1(1-460) and human Fc, named huBACE1:Fc, is con- structed into the pJB02 vector. Human BACE1(1-460):Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification. huBACE1: Fc is purified by Protein A chromatography. The enzyme is stored at −80° C. in small aliquots.

In Vitro Protease Inhibition Assays:

BACE1 FRET Assay

Serial dilutions of test compounds are prepared as described above. Compounds are further diluted 20× in KH$_2$PO$_4$ buffer. Ten µL of each dilution is added to each well on row A to H of a corresponding low protein binding black plate containing the reaction mixture (25 µL of 50 mM KH$_2$PO$_4$, pH 4.6, 1 mM TRITON® X-100, 1 mg/mL Bovine Serum Albumin, and 15 μM of FRET substrate) (See Yang, et. al., *J. Neurochemistry*, 91(6) 1249-59 (2004)). The content is mixed well on a plate shaker for 10 minutes. Fifteen μL of two hundred pM human BACE1(1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $IC_{50}$ values. (See Sinha, et al., *Nature*, 402, 537-540 (2000)).

The compounds of Examples 1-17 herein were tested essentially as described above and exhibited an $IC_{50}$ value for BACE1 of lower than about 1 μM. The following exemplified compounds were tested essentially as described above and exhibited the following activity for BACE1:

TABLE 21

| Example # | BACE1 $IC_{50}$ (nM) |
|---|---|
| 8 | 105 (±28.0, n = 5) |
| 12 | 73.4 (±13.8, n = 6) |
| 15 | 93.5 (±22.7, n = 4) |

Mean ± SEM;
SEM = standard error of the mean

These representative data demonstrate that the compounds of Table 21 potently inhibit purified recombinant BACE1 enzyme activity in vitro.

Whole Cell Assays for Measuring the Inhibition of Beta-Secretase Activity

HEK293Swe Whole Cell Assay

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn651Leu652, commonly called the Swedish mutation (noted HEK293/APP751sw) and shown to overproduce Abeta (Citron, et al., *Nature*, 360, 672-674 (1992)). In vitro Abeta reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293/APP751sw at $3.5 \times 10^4$ cells/well, containing 200 μL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $IC_{50}$ values for the Abeta-lowering effect. The following exemplified compounds were tested essentially as described above and exhibited the following activity for Abeta lowering effect:

TABLE 22

| Example | HEK 293 Swe A-beta (1-40) ELISA $IC_{50}$ (nM) | HEK 293 Swe A-beta (1-42) ELISA $IC_{50}$ (nM) |
|---|---|---|
| 8 | 242 | 395 |

These data demonstrate that the compound of Table 22 inhibits native endogenous human BACE1 in cells in vitro.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 μM (final) of Ara-C (Sigma, C1768). At day 5 in vitro, neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $IC_{50}$ values for the Abeta-lowering effect. The following exemplified compounds were tested essentially as described above and exhibited the following activity for Abeta lowering effect:

TABLE 23

| Example | PDAPP Neuron A-beta (1-40) ELISA $IC_{50}$ (nM) | PDAPP Neuron A-beta (1-42) ELISA $IC_{50}$ (nM) |
|---|---|---|
| 8 | 455 | 412 |
| 12 | 109 | 83.1 |
| 15 | 98.2 | 80.1 |

These data demonstrate that the compounds of Table 23 inhibit native, endogenous murine BACE1 in cells in vitro.

In Vivo Inhibition of Beta-Secretase

Several animal models, including mouse, rat, guinea pig, dog, and monkey, may be used to screen for inhibition of beta-secretase activity in vivo following compound treatment Animals used in this invention were transgenic PDAPP mice as described in Games et al., *Nature* 373, 523-527 (1995), which have been useful to analyze in vivo inhibition of Abeta production in the presence of inhibitory compounds. Two month old PDAPP mice are administered compound formulated in N-methylpyrolidone (Pharmasolve®) in water. Three hours following the administration of compound, animals are sacrificed, and brains are removed for analysis of Abeta fragments. (See Dovey, et al., *Journal of Neurochemistry*, 76, 173-181 (2001); and Johnson-Wood, et al., *Proc. Natl. Acad. Sci. USA*, 94, 1550-1555 (1997)).

For standard in vivo pharmacology studies, animals are dosed with various concentrations of compound and compared to a vehicle-treated control group dosed at the same time. At the end of the test period, animals are sacrificed and brain tissues are analyzed for the presence of Abeta peptides by specific sandwich ELISA assays. "Abeta 1-x peptide" as used herein refers to the sum of Abeta species that begin with residue 1 and end with a C-terminus greater than residue 28. This detects the majority of Abeta species and is often called "total Abeta".

Animals (PDAPP or other APP transgenic or non-transgenic mice) administered an inhibitory compound may demonstrate the reduction of Abeta in brain tissues as compared with vehicle-treated controls or time zero controls. For example, 3 hours after administration of a 10 mg/kg or 30 mg/kg oral dose of the compound of Example 8 to young female PDAPP mice, Abeta 1-x peptide levels are significantly reduced approximately 19% and 46% respectively in brain hippocampus, and approximately 23% and 53% respectively in brain cortex, compared to vehicle-treated mice. Significant and dose-responsive reduction of total Abeta after oral administration of the compound of Example 8 is consistent with a mechanism of BACE (the beta-secretase enzyme) inhibition in vivo. These studies show that compounds of the present invention inhibit BACE and are, therefore, useful in reducing Abeta levels. As such, compounds of the present invention are efficacious inhibitors of BACE.

We claim:
1. A compound of the formula:

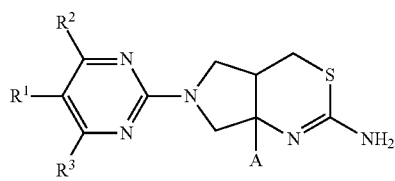

wherein A is selected from the group consisting of;

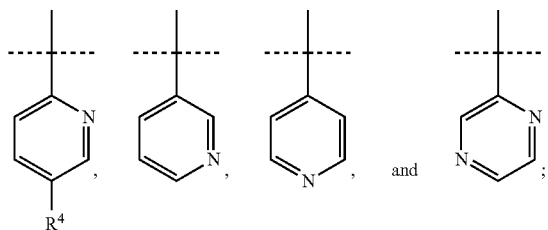

$R^1$ is H or F;
$R^2$ is H, —OCH$_3$, C1-C3 alkyl,

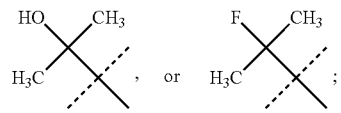

$R^3$ is H, —CH$_3$, or —OCH$_3$; and
$R^4$ is H or F;
or a pharmaceutically acceptable salt thereof.

2. A compound or salt according to claim 1 wherein A is selected from the group consisting of:

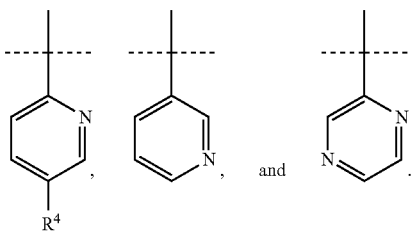

3. A compound or salt according to claim 2 wherein A is selected from the group consisting of:

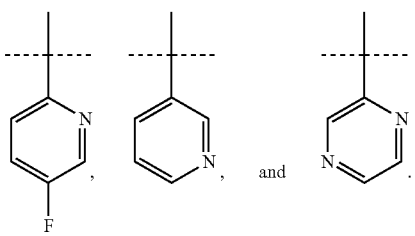

4. A compound or salt according to claim 3 wherein A is:

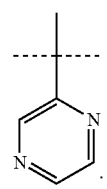

5. A compound or salt according to claim 4 wherein $R^2$ is

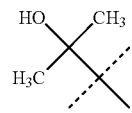

6. A compound or salt according to claim 5 wherein $R^1$ is F.
7. A compound or salt according to claim 1 which is 2-[2-[(4aR,7aR)-2-amino-7a-pyrazin-2-yl-4,4a,5,7-tetrahydropyrrolo[3,4-d][1,3]thiazin-6-yl]-5-fluoro-pyrimidin-4-yl]propan-2-ol.
8. A method of treating Alzheimer's disease in a patient, comprising administering to a patient in need of such treatment an effective amount of a compound of claim 1, or a pharmaceutically acceptable salt thereof.

9. A pharmaceutical composition, comprising a compound or a pharmaceutically acceptable salt thereof according to claim 1 with one or more pharmaceutically acceptable carriers, diluents, or excipients.

10. A pharmaceutical composition, comprising a compound or a pharmaceutically acceptable salt thereof according to claim 7 with one or more pharmaceutically acceptable carriers, diluents, or excipients.

11. A method of treating Alzheimer's disease in a patient, comprising administering to a patient in need of such treatment an effective amount of a compound of claim 7, or a pharmaceutically acceptable salt thereof.

* * * * *